US011887502B2

(12) United States Patent
Dantes et al.

(10) Patent No.: US 11,887,502 B2
(45) Date of Patent: Jan. 30, 2024

(54) SURGICAL SIMULATION CAMERA SCOPE

(71) Applicant: Applied Medical Resources Corporation, Rancho Santa Margarita, CA (US)

(72) Inventors: Richard Dantes, Rancho Santa Margarita, CA (US); Jacob Filek, Rancho Santa Margarita, CA (US); Jimmy Ho, Rancho Santa Margarita, CA (US); Sean Kenneday, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1353 days.

(21) Appl. No.: 16/230,689

(22) Filed: Dec. 21, 2018

(65) Prior Publication Data

US 2019/0206281 A1  Jul. 4, 2019

Related U.S. Application Data

(60) Provisional application No. 62/724,720, filed on Aug. 30, 2018, provisional application No. 62/613,696, filed on Jan. 4, 2018.

(51) Int. Cl.
*G09B 23/28* (2006.01)
*A61B 1/05* (2006.01)
(Continued)

(52) U.S. Cl.
CPC ............ *G09B 23/28* (2013.01); *A61B 1/0011* (2013.01); *A61B 1/00096* (2013.01);
(Continued)

(58) Field of Classification Search
CPC ...... G09B 23/28; G09B 23/285; G09B 23/30; A61B 1/00096; A61B 1/0011;
(Continued)

(56) References Cited

U.S. PATENT DOCUMENTS 4,491,865 A   1/1985 Danna et al.
4,600,938 A   7/1986 Sluyter et al.
(Continued)

FOREIGN PATENT DOCUMENTS

DE   102004023866 B3   2/2006
EP            1992968 A1 * 11/2008   ........... A61B 1/0019
(Continued)

OTHER PUBLICATIONS

The International Bureau of WIPO, International Preliminary Report on Patentability for International Application No. PCT/US2018/067310, entitled "Surgical Simulation Camera Scope," dated Jul. 16, 2020, 9 pgs.
(Continued)

*Primary Examiner* — Malina D. Blaise
*Assistant Examiner* — Andrew Bodendorf
(74) *Attorney, Agent, or Firm* — Thomas Nguyen; Patrick Ikehara

(57) ABSTRACT

A surgical simulation camera scope is provided. The surgical simulation camera scope comprises a lens mount with a lens and a sensor mount with an image sensor disposed between the sensor mount and the lens mount. The arrangement of the lens mount and the sensor mount ensures that the location of the sensor is maintained within the depth of focus of the lens while not damaging the sensor.

22 Claims, 18 Drawing Sheets

(51) Int. Cl.
  *A61B 1/313* (2006.01)
  *G02B 23/24* (2006.01)
  *A61B 1/00* (2006.01)
  *G09B 23/30* (2006.01)

(52) U.S. Cl.
  CPC .............. *A61B 1/051* (2013.01); *A61B 1/313* (2013.01); *G02B 23/2423* (2013.01); *G02B 23/2476* (2013.01); *G02B 23/2484* (2013.01); *G09B 23/285* (2013.01); *G09B 23/30* (2013.01)

(58) Field of Classification Search
  CPC ........... A61B 1/051; A61B 1/313; A61B 1/05; G02B 23/2423; G02B 23/2476; G02B 23/2484; H04N 23/55
  See application file for complete search history.

(56) References Cited

U.S. PATENT DOCUMENTS

| | | |
|---|---|---|
| 4,600,939 A | 7/1986 | Sluyter et al. |
| 4,600,940 A | 7/1986 | Sluyter |
| 4,639,772 A | 1/1987 | Sluyter et al. |
| 4,677,471 A | 6/1987 | Takamura et al. |
| 4,734,778 A | 3/1988 | Kobayashi |
| 4,918,521 A | 4/1990 | Yabe et al. |
| 4,947,245 A | 8/1990 | Ogawa et al. |
| 5,050,584 A | 9/1991 | Matsuura |
| 5,228,430 A | 7/1993 | Sakamoto |
| 5,325,847 A | 7/1994 | Matsuno |
| 5,379,756 A | 1/1995 | Pileski et al. |
| 5,594,497 A | 1/1997 | Ahern et al. |
| 5,711,756 A | 1/1998 | Chikama |
| 5,961,445 A | 10/1999 | Chikama |
| 5,966,168 A | 10/1999 | Miyazaki |
| 5,989,185 A | 11/1999 | Miyazaki |
| 6,117,071 A | 9/2000 | Ito et al. |
| 6,184,923 B1 | 2/2001 | Miyazaki |
| 6,478,730 B1 | 11/2002 | Bala et al. |
| 6,554,767 B2 | 4/2003 | Tanaka |
| 6,692,431 B2 | 2/2004 | Kazakevich |
| 6,796,939 B1 | 9/2004 | Hirata et al. |
| 7,063,663 B2 | 6/2006 | Kazakevich |
| 7,201,717 B2 | 4/2007 | Matsuura |
| 7,384,308 B2 | 6/2008 | Boehnlein et al. |
| 7,431,619 B2 | 10/2008 | Boehnlein et al. |
| 7,435,218 B2 | 10/2008 | Krattiger et al. |
| 7,581,988 B2 | 9/2009 | Boehnlein et al. |
| 7,584,534 B2 | 9/2009 | Pease et al. |
| 7,749,160 B2 | 7/2010 | Hirata |
| 7,878,972 B2 | 2/2011 | D'Amelio et al. |
| 7,976,459 B2 | 7/2011 | Laser |
| 8,154,810 B2 | 4/2012 | Barnes et al. |
| 8,218,074 B2 | 7/2012 | Pease et al. |
| 8,269,828 B2 | 9/2012 | Miller et al. |
| 8,308,637 B2 | 11/2012 | Ishigami et al. |
| 8,423,110 B2 | 4/2013 | Barbato et al. |
| 9,380,928 B2 | 7/2016 | Hu et al. |
| 9,565,993 B2 | 2/2017 | Okuda et al. |
| 9,585,813 B2 | 3/2017 | Dorsey et al. |
| 9,629,524 B2 | 4/2017 | Kaneko |
| 9,681,797 B2 | 6/2017 | Scherr et al. |
| 9,795,279 B2 | 10/2017 | Hogrefe et al. |
| 9,808,148 B2 | 11/2017 | Miller et al. |
| 2006/0004258 A1 | 1/2006 | Sun et al. |
| 2007/0162095 A1 | 7/2007 | Kimmel et al. |
| 2008/0027276 A1 | 1/2008 | Rovegno |
| 2008/0055403 A1* | 3/2008 | Salman ................. A61B 1/05 348/76 |
| 2009/0051763 A1* | 2/2009 | Adler .................. A61B 90/36 348/308 |
| 2009/0118580 A1 | 5/2009 | Sun et al. |
| 2010/0286476 A1 | 11/2010 | Jiang et al. |
| 2011/0134234 A1 | 6/2011 | Kim |
| 2015/0181086 A1* | 6/2015 | Pahlitzsch ............ H04N 23/52 348/374 |
| 2016/0000301 A1* | 1/2016 | Langell .............. A61B 1/00105 600/109 |
| 2016/0007833 A1* | 1/2016 | Huang ................ A61B 1/128 600/109 |
| 2016/0028929 A1* | 1/2016 | Nakamura ............ H04N 23/55 348/373 |
| 2016/0106303 A1 | 4/2016 | Birnkrant et al. |
| 2016/0316117 A1* | 10/2016 | Singh ................. H04N 23/54 |
| 2017/0059850 A1* | 3/2017 | Yashiro ............. G02B 23/2476 |
| 2017/0064249 A1* | 3/2017 | Kitano ................. A61B 1/051 |
| 2017/0319054 A1 | 11/2017 | Miller et al. |
| 2017/0339322 A1* | 11/2017 | Bauer .................... H04N 23/55 |
| 2019/0125168 A1* | 5/2019 | Kobayashi ......... A61B 1/00186 |
| 2020/0064618 A1* | 2/2020 | Kuchimaru ............ H04N 23/45 |

FOREIGN PATENT DOCUMENTS

| | | | |
|---|---|---|---|
| FR | 2751197 A1 * | 1/1998 | ......... A61B 1/00096 |
| JP | 2002291693 A | 10/2002 | |

OTHER PUBLICATIONS

European Patent Office, The International Search Report and Written Opinion for International Application No. PCT/US2018/067310, entitled "Surgical Simulation Camera Scope," dated Mar. 15, 2019, 49 pgs.

* cited by examiner

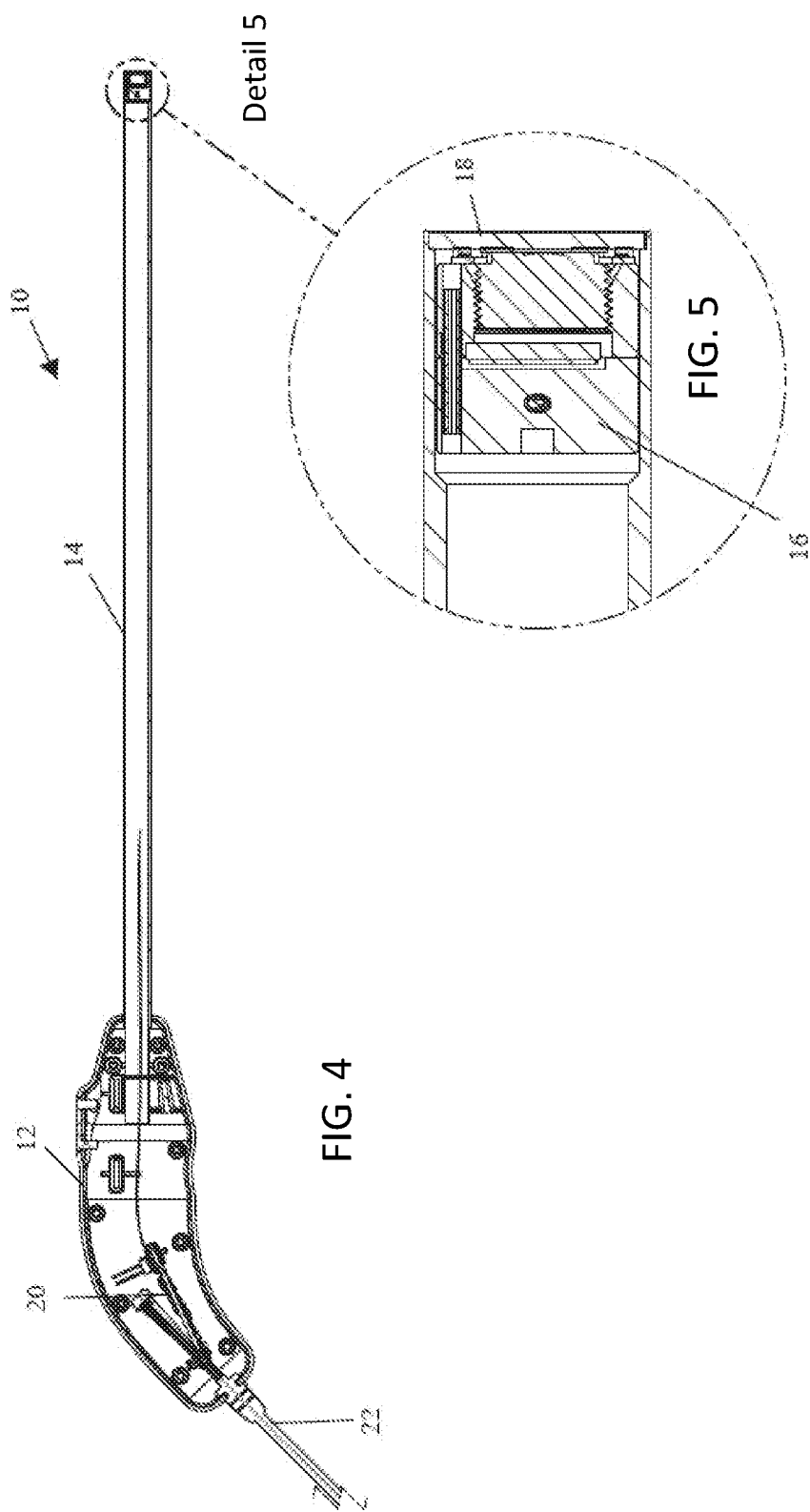

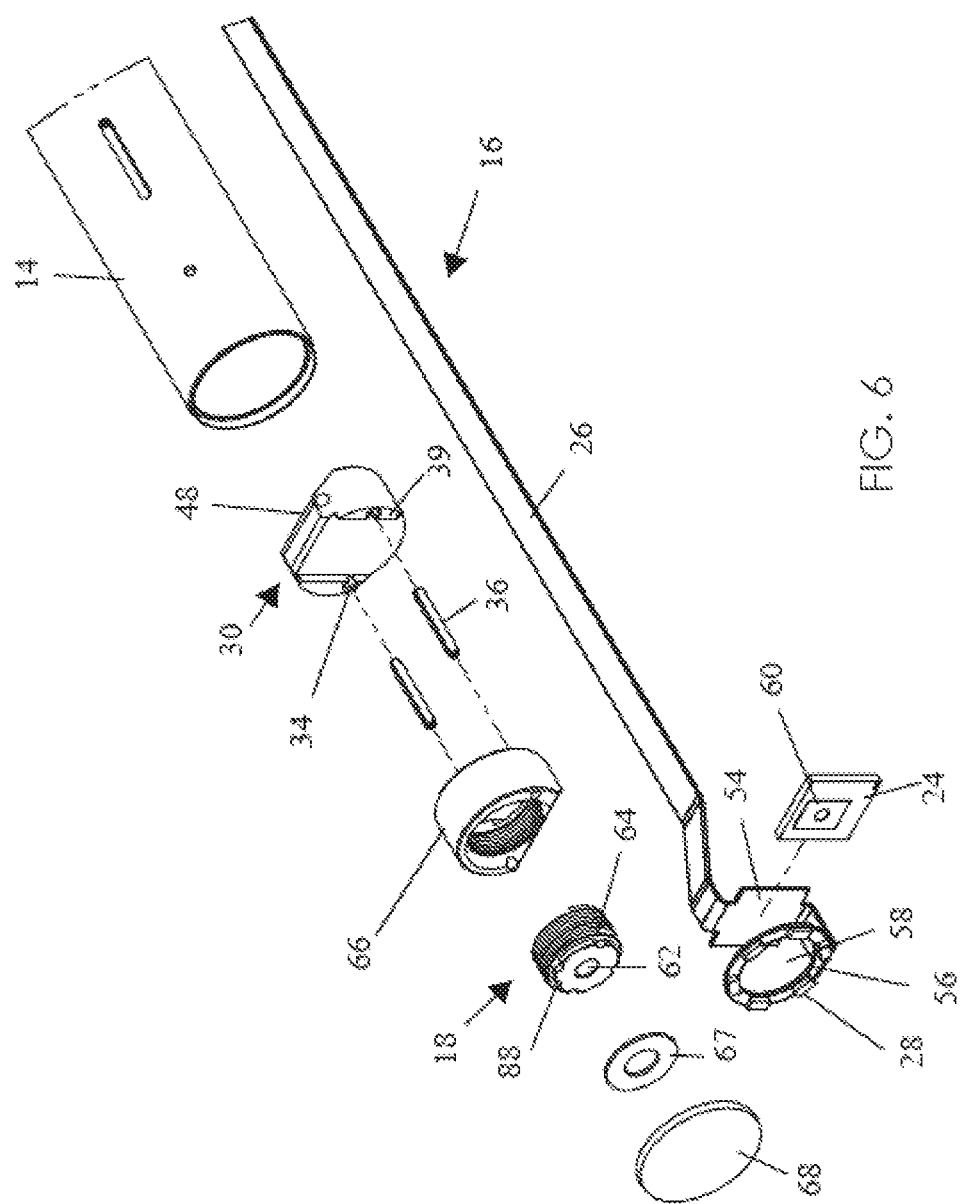

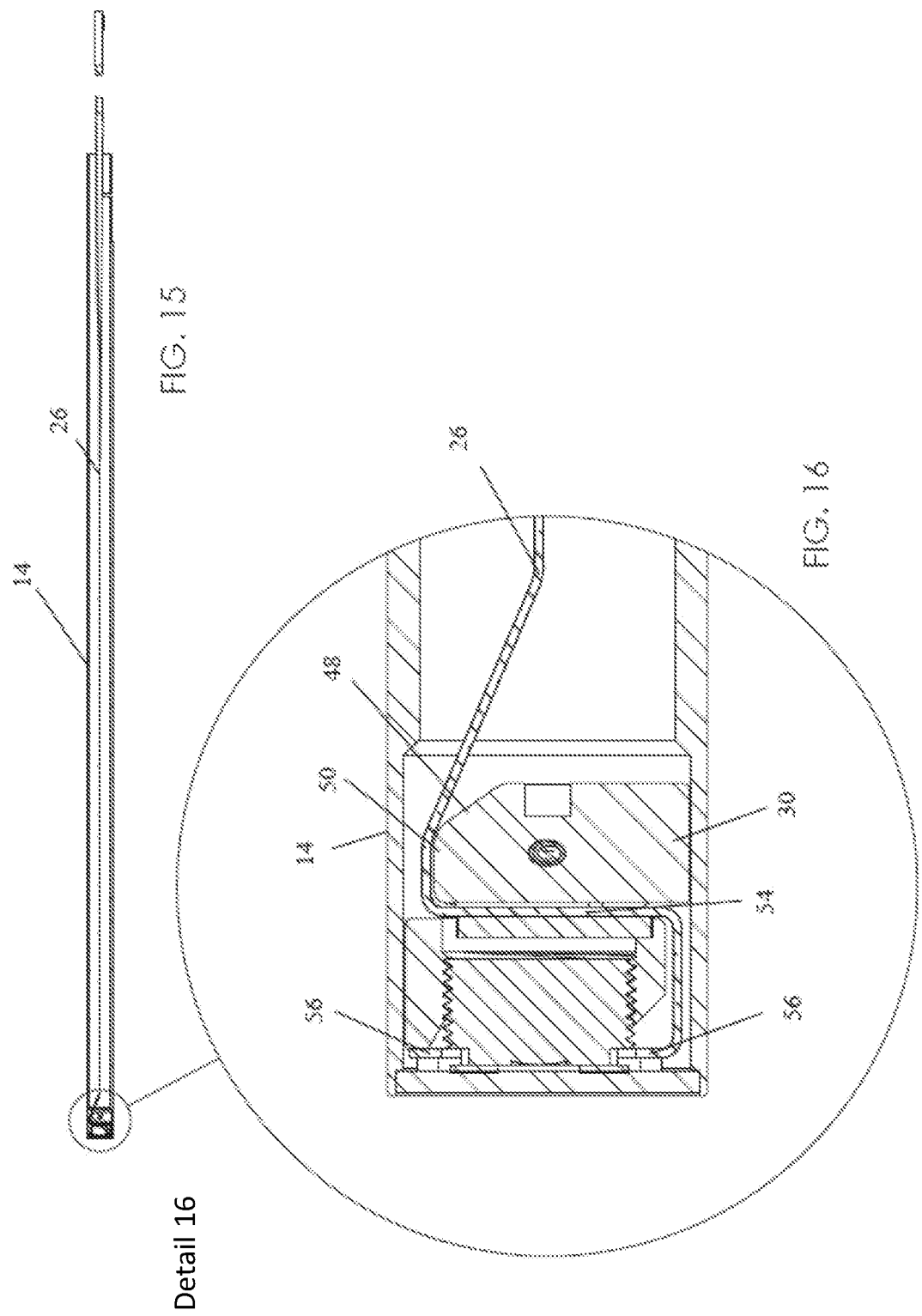

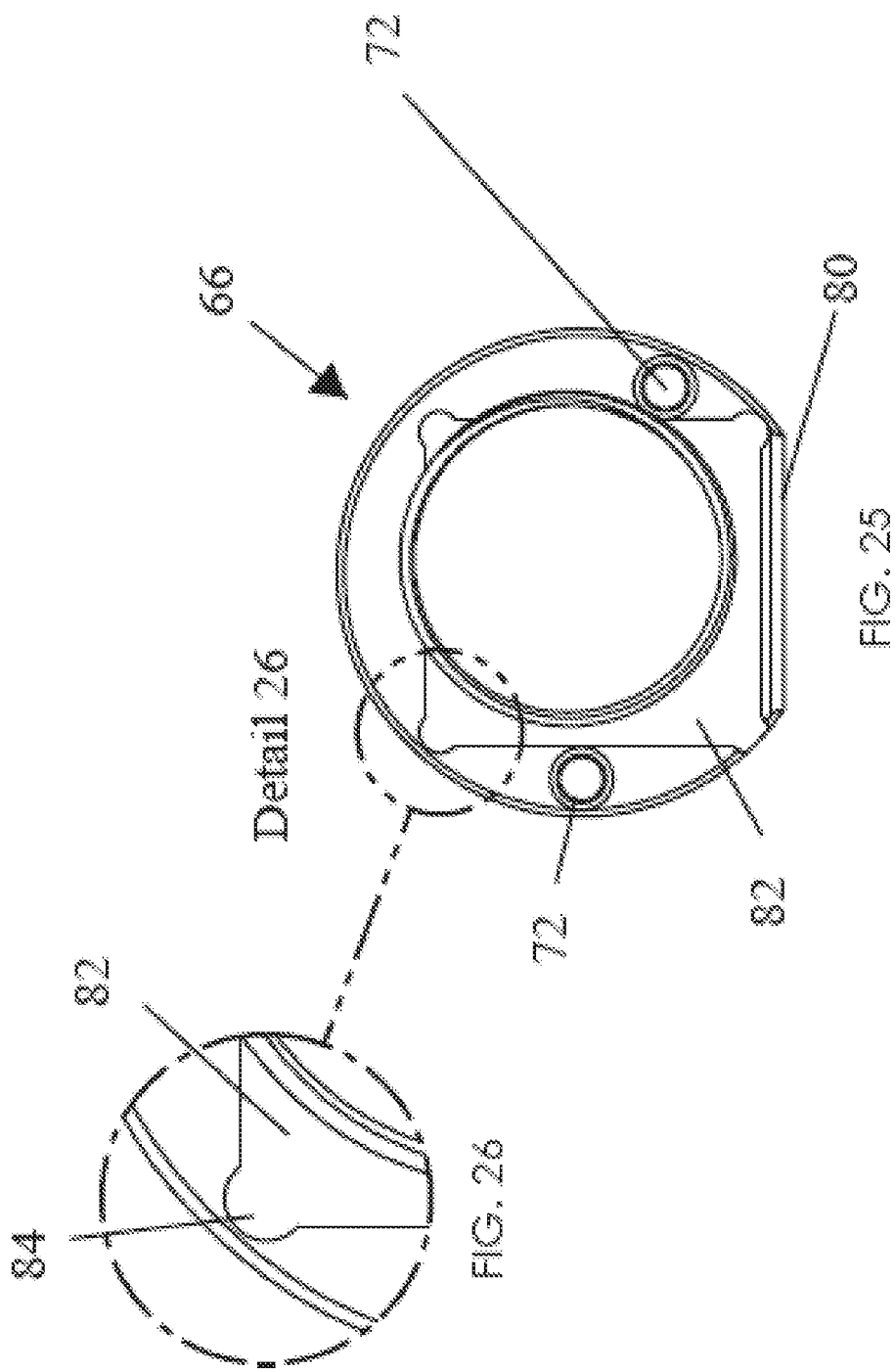

SECTION D-D

SURGICAL SIMULATION CAMERA SCOPE

CROSS-REFERENCE TO RELATED APPLICATIONS

This application claims the benefit of U.S. Provisional Application No. 62/613,696, filed on Jan. 4, 2018 and U.S. Provisional Application No. 62/724,720, filed on Aug. 30, 2018, the entire disclosures of which are hereby incorporated by reference as if set forth in full herein.

BACKGROUND

The present application relates generally to surgical simulation systems and methods and more particularly to surgical simulation camera scopes, systems and methods thereof.

Surgical scopes are used in endoscopic and laparoscopic procedures in which small incisions are employed to pass scopes and instruments, such as scissors, dissectors and graspers, into a cavity of the body at the surgical site. Surgery is performed while observing the site captured by a scope and displaying a live image feed on a video monitor for observation by the surgeon. As such, learning laparoscopic surgery is very difficult, as the surgeon does not observe the organs and tissues directly with the naked eye. Visual information is obtained indirectly via a monitor displaying a two-dimensional image. The loss of information when presenting a three-dimensional environment via a two-dimensional image is significant. In particular, depth perception is reduced when viewing a two-dimensional image as a guide for manipulating instruments in three dimensions. Furthermore, trocars are inserted through small incisions and rest against the abdominal wall. As a result, the manipulation of instruments/scopes is restricted by the abdominal wall, which has a fulcrum effect on the instrument/scope. Hence, hand-eye coordination skills are necessary and must be practiced in order to correlate hand motion with tool tip motion. The surgeon must also develop a set of core haptic skills because tactile sensation is diminished, as the surgeon cannot palpate the tissue directly by hand. The acquisition of all of these skills and more is a challenge in laparoscopic training and there is a need for scopes that are suitable for use in a training environment.

SUMMARY

Generally, a surgical simulation camera scope is provided. In various embodiments, the surgical simulation camera scope comprises a handle and an elongate shaft connected thereto. The elongate shaft at its distal end comprises a lens mount with a lens and a sensor mount with an image sensor disposed between the sensor mount and the lens mount. In various embodiments, the image sensor is connected to a flexible circuit board that extends from the image sensor to the handle.

In various embodiments, the surgical simulation camera scope comprises a handle and an elongate shaft connected thereto. The elongate shaft has a proximal end coupled to the handle and a distal end comprising a sensor mount and a lens mount. The lens mount in various embodiments has a proximal portion with a pocket therein and a lens is disposed within the lens mount. In various embodiments, an image sensor is disposed within the pocket of the lens mount and has a distal face facing the distal end of the elongate shaft.

In various embodiments, the surgical simulation camera scope comprises a handle and an elongate shaft connected thereto. The elongate shaft has a proximal end coupled to the handle and a distal end comprising a sensor mount and a lens mount. The elongate shaft in various embodiments has a longitudinal axis extending from the proximal end of the elongate shaft to the distal end of the elongate shaft. The surgical simulation camera scope, in various embodiments, further comprises a lens and an image sensor with the lens being disposed in a lens mount and the image sensor being disposed between the sensor mount and the lens mount. The lens mount, in various embodiments, has a proximal end and a distal end and the sensor mount has a proximal end and a distal end such that the proximal end of the sensor mount is parallel to the distal end of the sensor mount and the proximal end of the lens mount and orthogonal to the longitudinal axis of the elongate shaft.

In various embodiments, a simulation surgical camera scope is provided comprising at least one of a lens mount and/or a sensor mount. In various embodiments, a simulation surgical camera scope comprises a handle, a cylindrical elongate shaft having a proximal end coupled to the handle and a distal end. In various embodiments, the cylindrical elongate shaft comprises a cylindrical sensor mount and a cylindrical lens mount in which the cylindrical lens mount has threads disposed on an inner surface of the cylindrical lens mount. In various embodiments, a cylindrical lens has threads disposed on an outer surface of the lens and is arranged to mate with the threads of the cylindrical lens mount and the cylindrical lens mount has a pocket, a center aperture and/or at least one pin hole positioned next to the pocket. In various embodiments, an image sensor is disposed within the pocket of the cylindrical lens mount and between the cylindrical sensor mount and the cylindrical lens mount. In various embodiments, the cylindrical sensor mount has a cavity defined by a pair of raised surfaces and/or at least one of the pair of raised surface having at least one pin hole. In various embodiments, the at least one pin hole of the cylindrical lens mount is aligned with the at least one pin hole of the cylindrical sensor mount.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF THE DRAWINGS

The present inventions may be understood by reference to the following description, taken in connection with the accompanying drawings in which the reference numerals designate like parts throughout the figures thereof.

FIG. 4 is a cross-sectional view taken along line 4-4 of FIG. 3 of a surgical simulation camera scope in accordance with various embodiments of the present invention.

FIG. 5 is a partial cross-sectional view, detail 5 of FIG. 4, of the distal end of a surgical simulation camera scope in accordance with various embodiments of the present invention.

FIG. 6 is an exploded, top perspective view of a surgical simulation camera scope in accordance with various embodiments of the present invention.

FIG. 15 is a cross-sectional view taken along line 15-15 of FIG. 13 of a shaft, sensor assembly and lens assembly in accordance with various embodiments of the present invention.

FIG. 16 is a detail view of the distal end of a shaft, sensor assembly and lens assembly of FIG. 15 in accordance with various embodiments of the present invention.

FIG. 25 is a bottom view of a lens mount in accordance with various embodiments of the present invention.

FIG. 26 is a detailed view of detail 26 of FIG. 25 of a lens mount in accordance with various embodiments of the present invention.

DETAILED DESCRIPTION

Generally, a simulation surgical camera scope is provided to assist in laparoscopic surgical skill training and simulation. The environment for training laparoscopic surgical skills can include a box trainer that is intended to simulate the human abdominal area. The trainer in various embodiments includes a penetrable cover that simulates an abdominal wall through which surgical instruments and scopes are inserted to access the simulated body cavity that houses artificial organs or skills training models upon which mock surgical procedures are practiced. Real surgical or surgical-grade scopes may be employed in a training environment. Surgical-grade scopes are high quality, calibrated, precision instruments, have very limited optical distortion, and provide enough light to completely illuminate the cavity. Surgical-grade scopes however are also very expensive costing thousands of dollars. Because surgical-grade scopes are expensive and can be easily mishandled, damaged, and scratched by less experience users, there is a need for training scopes for use in a training environment. In addition, less expensive scopes and scopes that are more portable are needed, not only in a training environment, but also, in a marketing environment to showcase instruments and demonstrate new procedures on the go. Scopes of the same caliber as surgical-grade scopes are not needed in a training or marketing environment and may be too cumbersome and expensive to port. In addition, because budgets for surgical training and simulation centers are limited, there is a need for inexpensive yet effective scopes designed with training purposes in mind.

Figure 1:
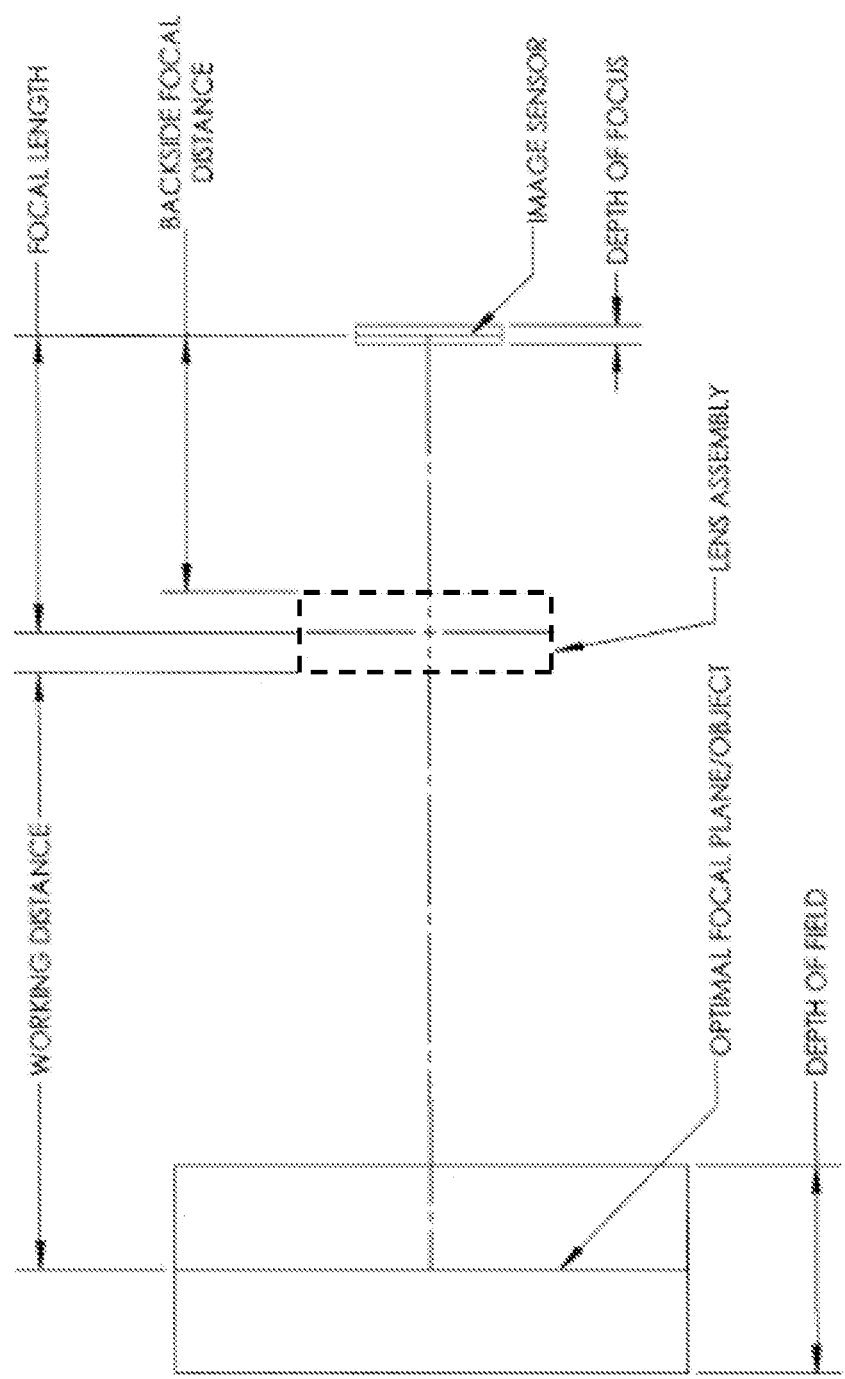
FIG. 1 is a schematic of an optical train and terms in accordance with various embodiments of the present invention.
Figure 2:
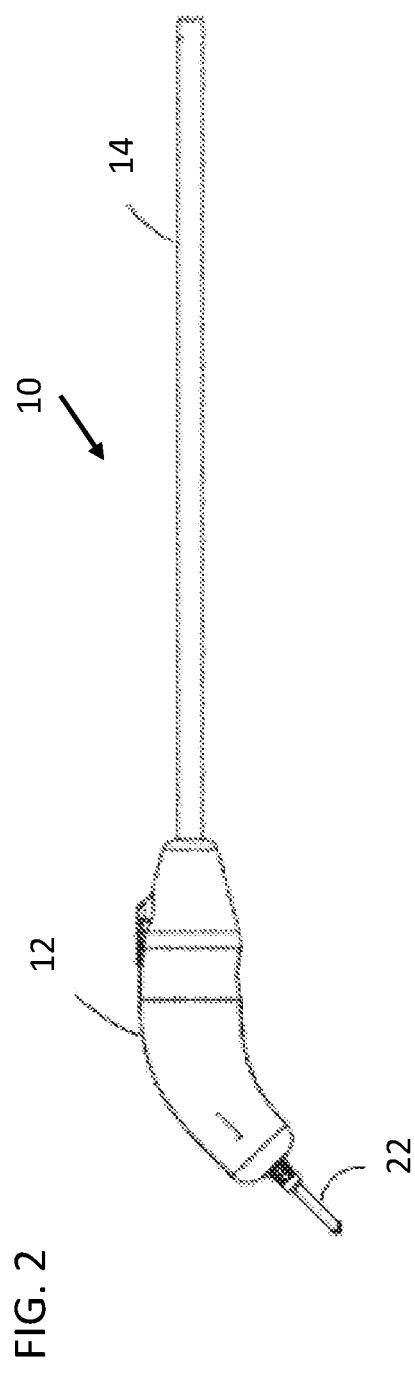
FIG. 2 is a side view of a surgical simulation camera scope in accordance with various embodiments of the present invention.
Figure 3:
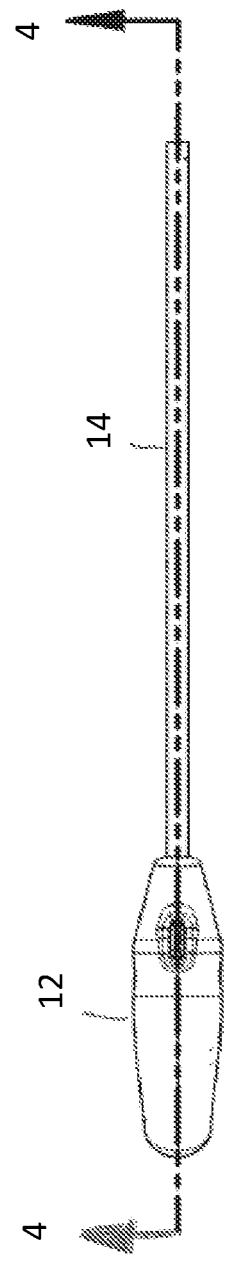
FIG. 3 is a top view of a surgical simulation camera scope in accordance with various embodiments of the present invention.
Figure 7:
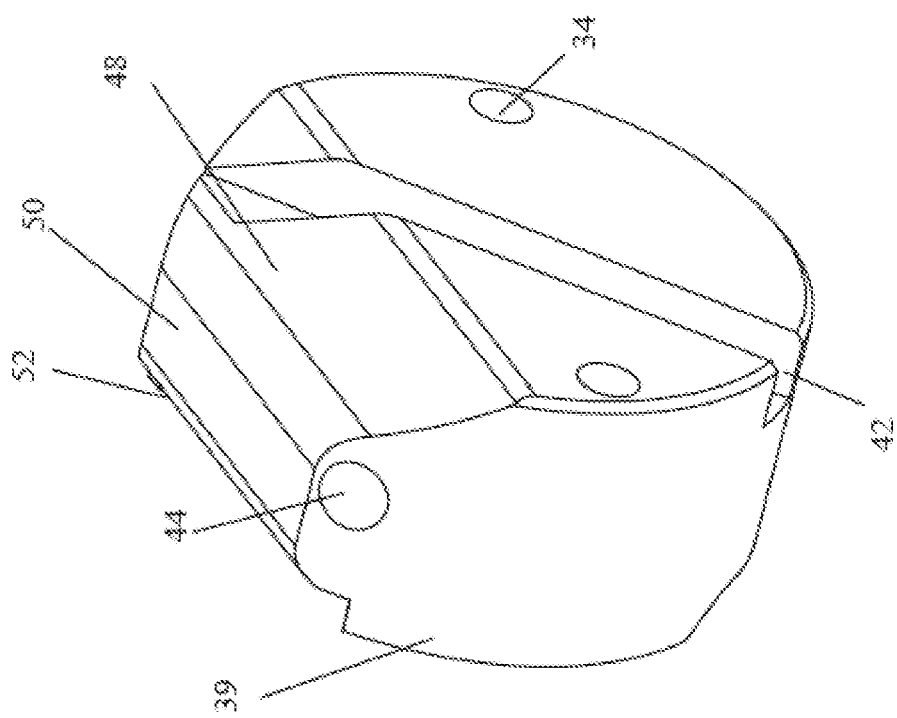
FIG. 7 is a top perspective view of a sensor mount in accordance with various embodiments of the present invention.

The optical performance of a simulation surgical scope should be similar to surgical-grade scopes with respect to certain characteristics. These characteristics include, but are not limited to, working distance, depth-of-field, field-of-view, image color and/or image quality. Some of these characteristics are schematically depicted in FIG. 1 for readability of the description and not a suggestion of prior art or admission of such. Image quality can include the sharpness of the video images in terms of pixel count resolution and the corresponding frames per second (fps) of the video feed. The simulation surgical scope in accordance with various embodiments provides an image quality that is approximately 640×480 to 720×1024 at approximately 24-60 fps. With respect to image color, the simulation surgical scope in accordance with various embodiments provides an approximate to the actual colors of an object when observed with the naked eye. Hence, the lighting employed at the tip of the training scope should not distort the colors of the organ models so that the realism of the simulation is not compromised. The working distance, which is the distance from the lens to the optimal focal plane is shown in FIG. 1, which is the plane of best focus. Still referencing FIG. 1, the depth-of-field is defined as the distance away from the optimal focal plane in both directions in which the image is still in focus. The depth-of-field should be as wide as possible. The field-of-view is defined as the area in the displayed image at the working distance. These and other characteristics work together to make for an image that is suitable for a simulation surgical scope in accordance with various embodiments of the present invention. Also, these parameters can provide the image, size, magnification, and/or other similar characteristics that correspond to a surgical-grade scope so that the trainee is not surprised when switching from the simulation surgical scope to using a surgical-grade scope.

With reference to FIGS. 2-6, the scope 10 in accordance with various embodiments includes a handle 12 connected to an elongated shaft 14. A sensor assembly 16 and lens assembly 18 are located inside the scope 10 and connected to the elongated shaft 14. The sensor assembly 16 is connected to a controller printed circuit board assembly (PCBA) 20 located inside the handle 12. The scope 10 is connectable to a computer or video monitor wirelessly or via a cable 22, such as a USB cable, and configured to display the captured video image.

With particular reference to FIG. 4, the handle 12 is a two-piece, clamshell design that defines an interior and houses the controller PCBA 20. The PCBA is connected to the sensor assembly 16 and to an output cable 22 that is in turn connected to a computer or video monitor in order to display a video image captured by a sensor and processed by a microcontroller on the controller PCBA. The elongated shaft 14 is connected to the distal end of the handle 12. In various embodiments, the handle 12 is provided with one or more buttons connected to a microcontroller on the PCBA to control the power and lighting of the scope 10. The lumen of the elongated shaft 14 opens to the interior of the handle 12 in order to connect the sensor assembly 16 to the PCBA 20.

Figure 17:
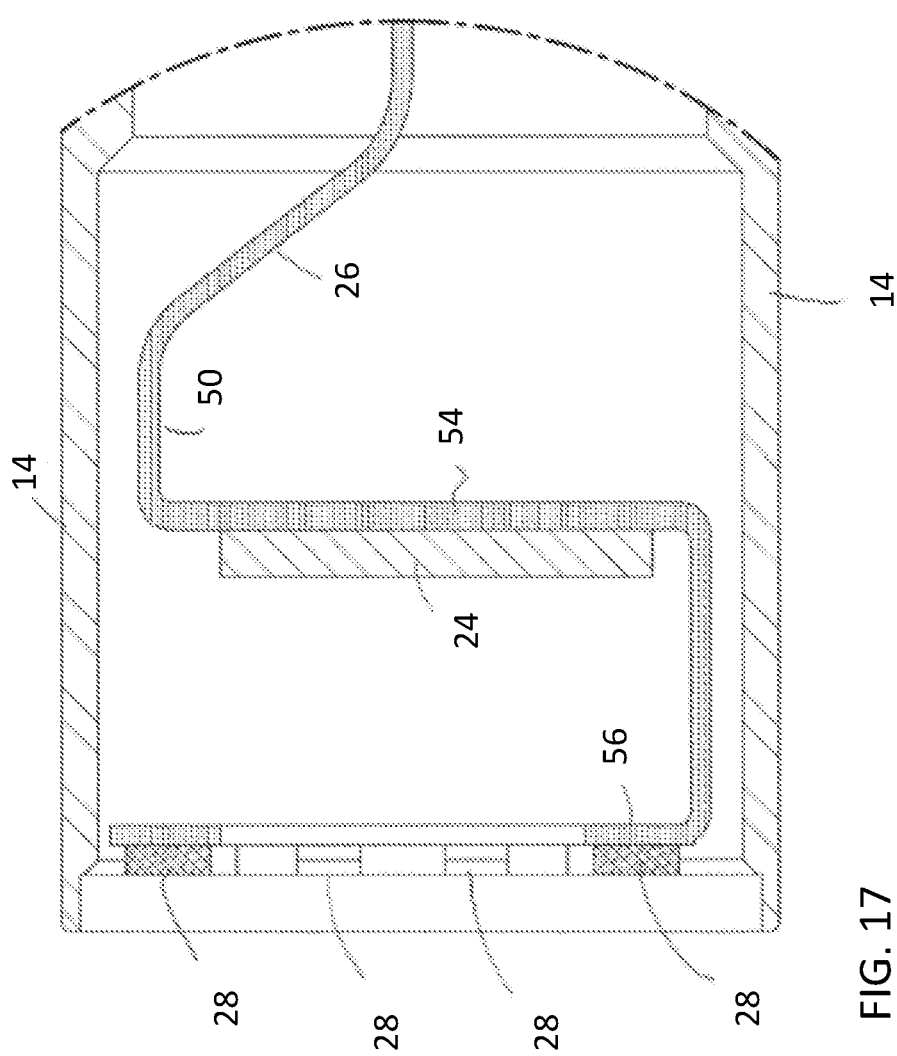
FIG. 17 is a partial, sectional view of a shaft, sensor, lights and flexboard in accordance with various embodiments of the present invention.

The elongated shaft 14 includes a sidewall having a cylindrical shape defining a lumen. The shaft 14 includes a proximal end and a distal end. The proximal end of the shaft 14 is connected to the handle 12 and includes a proximal opening such that the lumen of the shaft 14 opens to the interior of the handle 12. The distal end of the shaft 14 includes a distal opening. The diameter of the shaft 14 is approximately between 3 mm to 15 mm. The outside diameter is sized to fit inside a correspondingly sized trocar. For example, if the outside diameter of the shaft 14 is 10 mm, the inside diameter of the trocar is greater than 10 mm. The inner diameter of a 10 mm shaft 14 is approximately 8 mm. Hence, in such a variation, the diameter of the sensor is less than 8 mm so that it fits inside the shaft. Not only is the outer diameter sized to fit inside a corresponding trocar, but also, the inner diameter of the shaft 14 is sized to receive a sensor inside the shaft 14. In one variation, the inner diameter of the shaft 14 has a larger inner diameter at the distal end relative to the proximal end of the shaft 14 in order to house a larger sensor. For example, a shaft 14 with an inner diameter of approximately 8 mm is machined to be larger, approximately 9 mm at the distal end of the shaft 14 in order to fit a 9 mm sensor. Hence, the inner diameter of the shaft is stepped to a larger diameter at the distal end relative to the inner diameter at the proximal end as can be seen in FIGS. 16-17. The length of the shaft 14 is approximately 30-36 cm. The length from the handle 12 to the distal end of the shaft 14 is approximately 33 cm.

With additional reference to FIGS. 6-13, the sensor assembly 16 will now be described in greater detail. The sensor assembly 16 includes a sensor 24 and lights 28 mounted on an electrical connector 26. The sensor assembly 16 further includes a sensor mount 30. The sensor mount 30 is connected to the elongated shaft 14 via an indexing, mounting pin 32.

Figure 8:
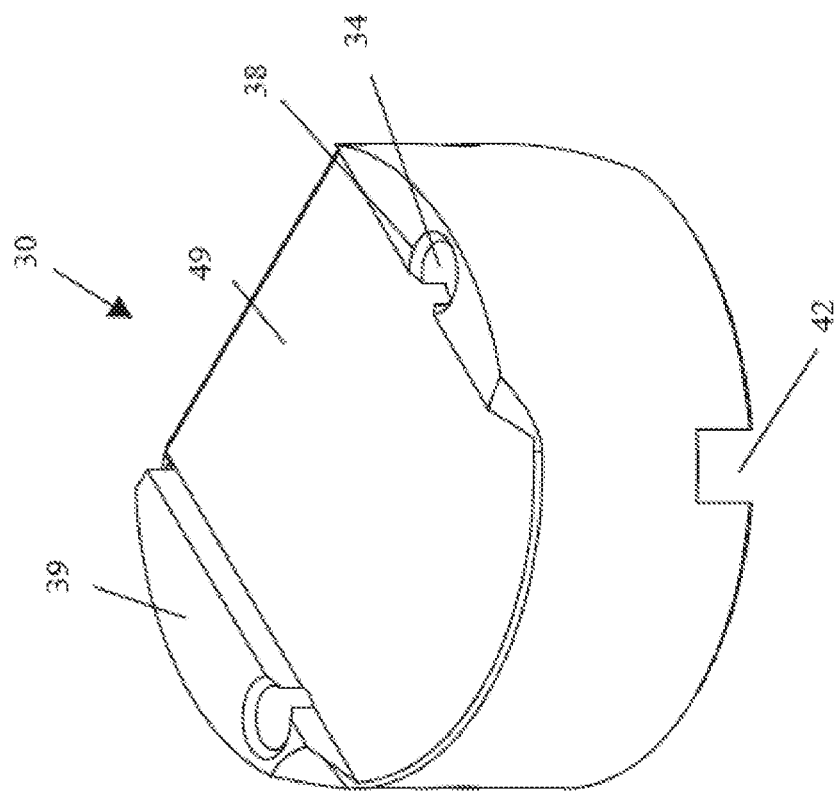
FIG. 8 is a top perspective view of a sensor mount in accordance with various embodiments of the present invention.
Figure 11:
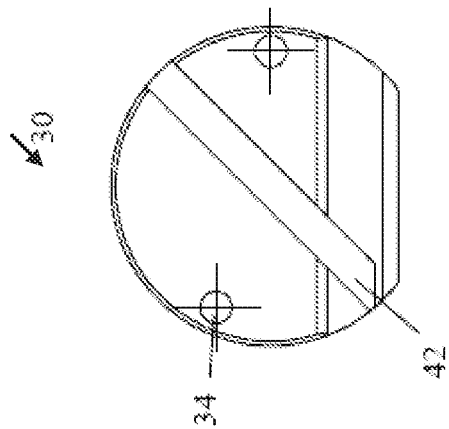
FIG. 11 is an end view of a sensor mount in accordance with various embodiments of the present invention.
Figure 10:
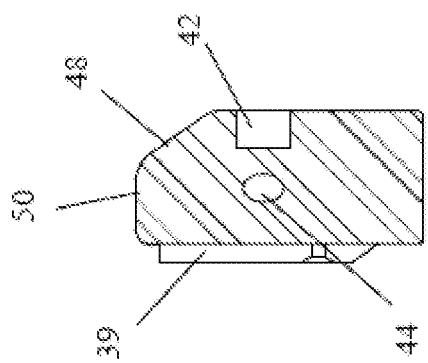
FIG. 10 is a cross-sectional view taken along line 10-10 of FIG. 9 of a sensor mount in accordance with various embodiments of the present invention.
Figure 12:
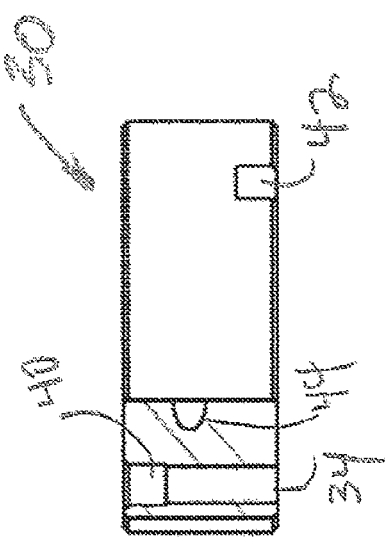
FIG. 12 is a cross-sectional view of a sensor mount in accordance with various embodiments of the present invention.
Figure 13:
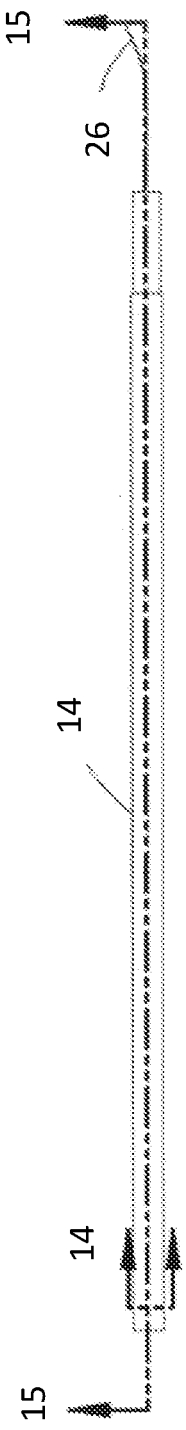
FIG. 13 is a side elevation view of a shaft, sensor assembly and lens assembly in accordance with various embodiments of the present invention.

With continued reference to FIGS. 6-13, the sensor mount 30 will now be described in greater detail. The sensor mount 30 is sized and configured to provide a backing and support for the sensor 24 and connector 26. The sensor mount 30 is partially cylindrical in shape and is sized to fit closely within the lumen of the elongated shaft 14. The sensor mount 30 has a proximal end and a distal end interconnected by a sidewall. Two pin holes 34 are provided extending parallel to the longitudinal axis of the shaft 14. The pin holes 34 extend between the proximal end and the distal end and are sized and configured to receive a pin 36' or dowel 36 in each pin hole 34. Each pin hole 34 includes a beveled entry 38 at the distal end of the pin hole 34 as can be seen in FIG. 8. The beveled entry 38 is a ramped or tapered entryway to facilitate insertion of a pin 36' or dowel 36 into the pin hole 34. In various embodiments, the distal end of the pin hole 34 includes a length 40 of the pin hole 34 having a diameter that is slightly larger than the diameter of the pin hole 34 at the proximal end as can be seen in FIG. 12.

In various embodiments, the dowel to pin hole interface is a slip fit arrangement, e.g., the diameter of the hole 34 is larger than dowel 36. This locates the sensor mount and the lens mount to each other in the radial directions, but allows movement in the axial direction. When the assembly is ready, glue is placed on the dowel and hole interface on the backside of the sensor mount to prevent the sensor mount from separating from the lens mount. It should be noted that care is taken before the application of the adhesive to ensure that the sensor mount and lens mount are aligned both radially and axially before permanently affixed together. It has been found that affixing the alignment of the sensor and lens mount in one direction, e.g., radial, first and then adjusting the sensor and lens mount in another direction, e.g., axial, ensures optimal alignment of the sensor and lens mount. It has also been found that allowing movement or adjustment of the sensor and lens mounts axially provides a precise placement of the sensor relative to the lens to ensure the sensor is within the depth of focus of the lens. Placement of the sensor outside of this range degrades image quality or inoperability of the scope. Likewise, any radial and skewed placement of the sensor also degrades image quality. Additionally, the relaxed or slip fit arrangement allows the coupling of the sensor and lens mount to be precise by avoiding friction and in particular friction that can cause sudden axial movement as the sensor and lens mounts are coupled together. Sudden axial movement or imprecise axial coupling of the sensor and lens mounts together can cause damage to the sensor and thus cause the scope to be inoperable.

Figure 9:
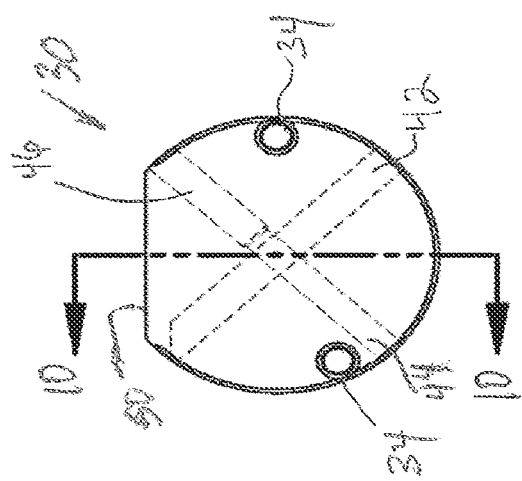
FIG. 9 is an end view of a sensor mount in accordance with various embodiments of the present invention.

Another pin hole 44 that is traverse to the longitudinal axis of the elongated shaft 14 is provided in the sensor mount 30 and extends through the sensor mount 30 between the sidewall. As can be seen in FIG. 9, the traverse pin hole 44 also includes an enlarged diameter portion 46 to facilitate insertion of a pin 32 as well as alignment and setting of the sensor mount 30 with respect to the elongated shaft 14. The pin 32 is longer than the dowel 36 or pin 36' employed in pin holes 34.

The proximal end of the sensor mount 30 includes a channel-like groove 42 sized and configured to receive an instrument such as a flat-head screwdriver. The groove 42 assists in the installation of the sensor mount 30 within the elongated shaft 14. During assembly, an instrument can be inserted into the groove 42 in order to help hold and move the sensor mount 30 into the lumen of the elongated shaft 14, hold the sensor mount 30 in position inside the elongated shaft 14, rotate the sensor mount 30 with respect to the elongated shaft 14, align the sensor mount 30 with respect to corresponding pin holes formed in the elongated shaft 14, and/or generally hold the sensor mount 30 stationary with respect to elongated shaft 14. The proximal end of the sensor mount 30 is substantially parallel to the distal end of the sensor mount 30. The proximal end of the sensor mount 30 also includes an angled surface 48 interconnected with a flat portion 50 of the sidewall. The angled surface 48 together with the flat portion 50 provide a landing and pathway for the connector 26 extending proximally inside the elongated shaft 14 to the PCBA 20 located in the handle 12. The distal end of the sensor mount 30 includes a bevel 52 at the intersection of the distal end with the flat portion 50 of the sidewall. The bevel 52 helps to provide a smooth bend in the connector 26 to prevent a sharp bend and associated stress concentrations in the connector 26.

In various embodiments, the distal end of the sensor mount also includes raised surfaces 39 disposed on either side of a middle, flat cavity or surface 49. The sensor and connector 26 are positioned on the middle, flat surface 49 of the sensor mount 30. It has been found that due to the limitations in size and dimensions of the distal end of the scope and the need for the precise placement of the sensor relative to the lens, the sensor is often crushed or damaged between the sensor and lens mounts. As such, raised surfaces 39 act as a hard stop to prevent crushing of the sensor between the sensor mount and lens mount. Thus, the dimensions and tolerance of the raised surfaces relative to the middle surface are such that when the sensor mount and lens mount are coupled or connected together with the sensor and connector between them, the sensor is not crushed. Additionally, there is a gap of 0.0015" or less between the flexboard assembly and the sensor mount and in various embodiments that is also accommodated by the raised surfaces. Accordingly, in accordance with various embodiments, the sensor and/or lens mount are configured to ensure that the spacing between the lens and sensor mounts is greater than the thickness of the sensor and the flexible printed circuit board and yet smaller than or no greater than the depth of focus range of the lens thereby ensuring the sensor is always located within the depth of focus, ensuring image quality is maintained and the sensor is not damaged. As such, in various embodiments, the height of the raised surface relative to the middle surface of the sensor mount is not greater than the depth of focus range of the lens.

In accordance with other various embodiments, the light sensing portion of the sensor is indexed to the lens mount to keep the crucial distance between the sensor and lens consistent. When assembling, the sensor mount without raised surfaces and the lens mount are brought together with less pressure than would crush the sensor. Force or pressure gauges or other similar force or pressure limiting components would be utilized to ensure that the threshold crush pressure of the sensor is not exceeded. Once in place, i.e., the sensor is located within the depth of focus of the lens, the mounts are affixed together, e.g., glued to the pins, preventing axial movement of the mounts relative to the sensor. In various other embodiments, the raised surfaces extends further from the middle surface, i.e., have a greater height or are larger in the axial direction, resulting in a bigger gap or spacing between lens and sensor mounts when assembled. To index the sensor to the lens mount, a mechanical spring or a material with spring like attributes, like silicone, is placed in the gap or spacing that is created by the raised surfaces, thus taking up the resulting gap of having the raised surfaces further from the middle, flat surface. In various embodiments, the sensor can be indexed, with a set screw coming from the proximal end of the sensor mount or similarly through the use of shim stock, to push the sensor against the lens mount.

In various embodiments, the connector 26 is a flexible circuit board or flexboard 26. The flexboard 26, in one embodiment, is approximately 17 inches long, approximately 0.10 inches wide and approximately 0.015 inches thick. The flexboard 26 is a connective device that provides an electrical connection between electrical components. In the present invention, the flexboard 26 is connected to the sensor 24 and lights 28, extends along the length of the shaft 14 and connects to the PCBA 20 inside the handle 12. The flexboard 26 reduces wiring errors during assembly, reduces assembly time and costs, eliminates mechanical connectors and provides design flexibility including highly complex configurations and provides a support for surface mounted devices. The flexboard 26 can be made to conform to a desired shape and flex during use and installation. The flexboard 26 is substantially planar and is connected at its proximal end to the PCBA 20 inside the handle 12. The flexboard 26 extends distally inside the shaft 14 as can be seen in FIG. 15. The flexboard 26 will twist approximately 90 degrees within the shaft 14 to facilitate connection with the sensor assembly 16 at the distal end and the PCBA 20 at the proximal end.

Figure 14:
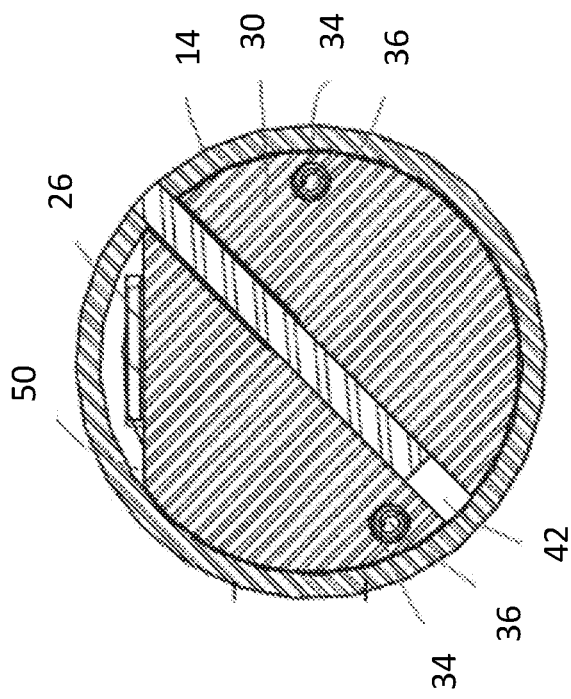
FIG. 14 is a cross-sectional view taken along line 14-14 of FIG. 13 of a shaft, sensor assembly and lens assembly in accordance with various embodiments of the present invention.
Figure 19:
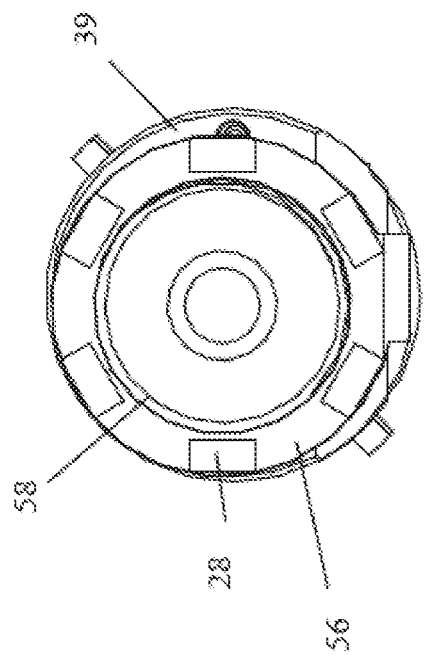
FIG. 19 is a sectional end view of the scope in accordance with various embodiments of the present invention.
Figure 18:
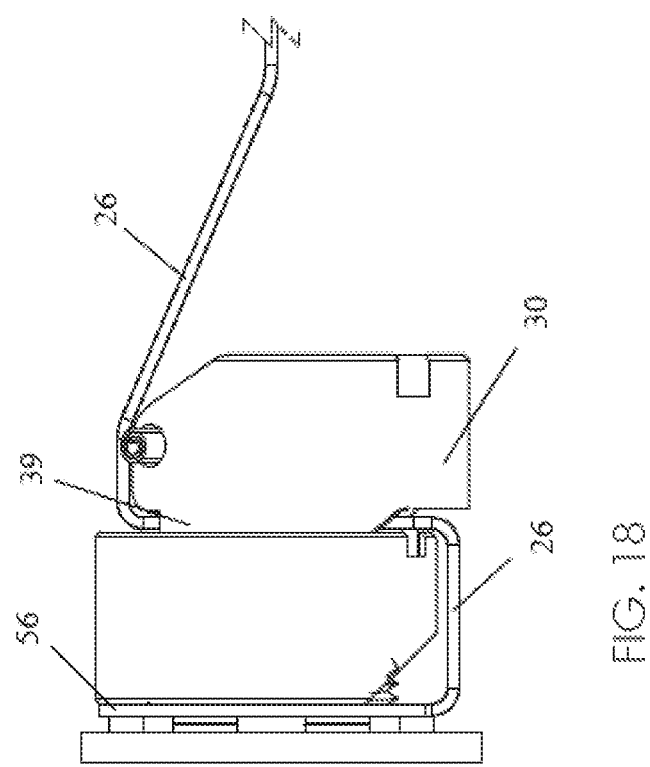
FIG. 18 is a partial sectional view of a sensor assembly and lens assembly in accordance with various embodiments of the present invention.

With particular reference to FIGS. 16 and 18, the flexboard 26 makes contact with the angled surface 48 of the sensor mount 30. The flexboard 26 is directed to pass over the flat portion 50 of the sidewall. The flat portion 50 advantageously reduces the diametrical distance of the sensor mount 30 to accommodate the thickness of the flexboard 26 as can be seen in FIG. 16 and in the FIG. 14. The flexboard 26 may be adhered with adhesive to the flat portion 50. From the flat portion 50, the flexboard 26 turns to extend along the distal end of the sensor mount 30. The flexboard 26 in one embodiment may be adhered to the distal end of the sensor mount 30. The distal end and proximal end of the sensor mount 30 are perpendicular to the longitudinal axis of the shaft 14. The flexboard 26 is also substantially perpendicular to the longitudinal axis of the shaft 14 along the distal end of the sensor mount. This perpendicular and flat portion of the flexboard 26 along the distal end of the sensor mount 30 is called a sensor location 54. It is at this location that the sensor 24 is connected to the flexboard 26 as can be seen in FIGS. 16-17. The sensor location 54 has an enlarged flat area compared to the flexboard 26 that is proximal to the sensor location. After the distal end of the sensor mount 30, the flexboard 26 makes an approximately 90 degree bend and extends distally before bending approximately 90 degrees to form a lighting or LED location 56 that is also approximately perpendicular to the longitudinal axis of the shaft 14. The lighting or LED location 56 of the flexboard 26 is where the lights/LEDs 28 are connected to the flexboard 26. The LED location 56 is flat and includes a central opening 58 as can be seen in FIGS. 6 and 19. The central opening 58 permits unobstructed and illuminated viewing via the lens assembly 18. In one variation, the lights 28 are a plurality of LEDs connected to the flexboard 26 with electrically conductive solder or adhesive and arranged in a circle around the central opening 58 and around the lens prior to assembly with the rest of the scope components. The flexboard 26 forms an S-shaped pathway as can be seen in FIGS. 16-18.

The flexboard 26 includes electrical contacts for the LEDs 28 and image sensor 24 and traces that allow power and data to be transmitted to the controller PCBA 20. The flexboard 26 also locates the LEDs 28 and image sensor 24 for assembly with the rest of the components in the shaft 14. The flexboard 26 eliminates the use of wires, is flat and smaller than an equivalent wire bundle it is replacing and can be designed and configured to meet the confines of the shaft dimension and assembly components. Furthermore, due to the sensor 24 being placed at the distal end of the scope and the controller PCBA 20 being positioned at the proximal end of the scope and the speed and/or amount of data being transmitted, the signal integrity between the components can degrade. However, the flexboard 26, in various embodiments, being a single monolithic component ensures that signal integrity of data transfer from the image sensor 24 is not compromised. In various embodiments, the flexboard includes, integrated or attached, a metallic layer, e.g., a copper only layer, to ensure signal integrity is maintained. The metallic layer is sized and dimensioned in various embodiments to shield the flexboard from outside electrical noise that can interfere with the signals transmitted through the traces on the flexboard, especially the high speed data lines. The flexboard 26 is sufficiently flexible to navigate the S-shaped pathway making multiple approximately 90-degree bends to meet the design of the sensor assembly 16 and lens assembly 18.

A ring of LEDs 28 are employed in the sensor assembly 16 and arrayed around the lens assembly as can be seen in FIG. 19. The LEDs 28 serve to illuminate the target object and surgical field. Approximately, 4-8 white LEDs 28 are used depending on the brightness required for a particular application or to allow use in all conditions including confined procedures such as transanal minimally invasive surgery (TAMIS) which may require more lighting. The LEDs may be selected to have an appropriate color temperature, or tinted, e.g., via tinted glass 67, to optimize color matching.

The sensor 24, in one embodiment, is a CMOS image sensor such as one produced by OmniVision Technologies, Inc. It is a ¼ sensor sized to fit within a 10 mm shaft 14. The sensor 24 supports video quality maximums of 720 pixels at 60 fps and has a resolution of 640×480 characteristic of the VGA hardware at 90 fps. The sensor 24 supports a video output format of YUV422 and has inter-integrated circuit communications to communicate with a microprocessor and has a camera serial interface 2 (CSI-2) mobile industry processor interface (MIPI) for the video communications. Sensors that would be small enough to fit within a 5 mm tube do not have the associated microprocessor, electronics and demosaicing algorithm to output in YUV422. Therefore, a separate circuit board would be needed to support a microprocessor and associated algorithm external to the sensor. The sensor 24 in various embodiments has a smaller active image area 60 comprising the array of photo sites. The sensor 24, which is not limited to a CMOS type sensor, is adhered with solder or electrically conductive adhesive to the flat sensor location 54 on the flexboard 26.

With reference to FIGS. 6 and 20-28, the lens assembly 18 will now be described. The lens assembly 18 in accordance with various embodiments includes a lens 62, a lens housing 64, a lens mount 66, a tinted glass 67, a cover glass 68 and/or combinations thereof. The lens 62 in various embodiments may include one or more lenses and optical elements. In various embodiments, the lens 62 includes an optical train having four lenses and an infrared filter. The lens 62 has a 3.8 mm focal length and is aspheric and achromatic. This configuration provides a working distance of approximately 50-70 mm, a depth-of-field of approximately 90-150 mm and a field-of-view of 60-65 degrees. Also, this configuration minimizes optical distortion while keeping costs down. The optical distortion is limited to the edges of the optical image. Since the diagonal dimension of the image area 60 of the sensor 24 is smaller than the diagonal of the focused optical image hitting the sensor, the distorted edges are not picked up by the sensor giving a clean non-distorted image on the monitor. The lens 62 is connected to and located inside the lens housing 64. The lens housing 64 is cylindrical in shape and includes an outer surface that is threaded. The threads are configured for threaded engagement with the lens mount 66. Although threads are employed, other types of fasteners are within the scope of the present invention so long as the lens is axially movable along the longitudinal axis with respect to the lens mount 66. The lens housing 64 further includes one or more notch, socket or the like 88 configured for receiving a distal end of a correspondingly shaped instrument. The instrument is inserted into the notch/socket 88 of the lens housing 64 in order to rotate the lens housing 64 with respect to the lens mount 66 for optically tuning the lens assembly.

Figure 21:
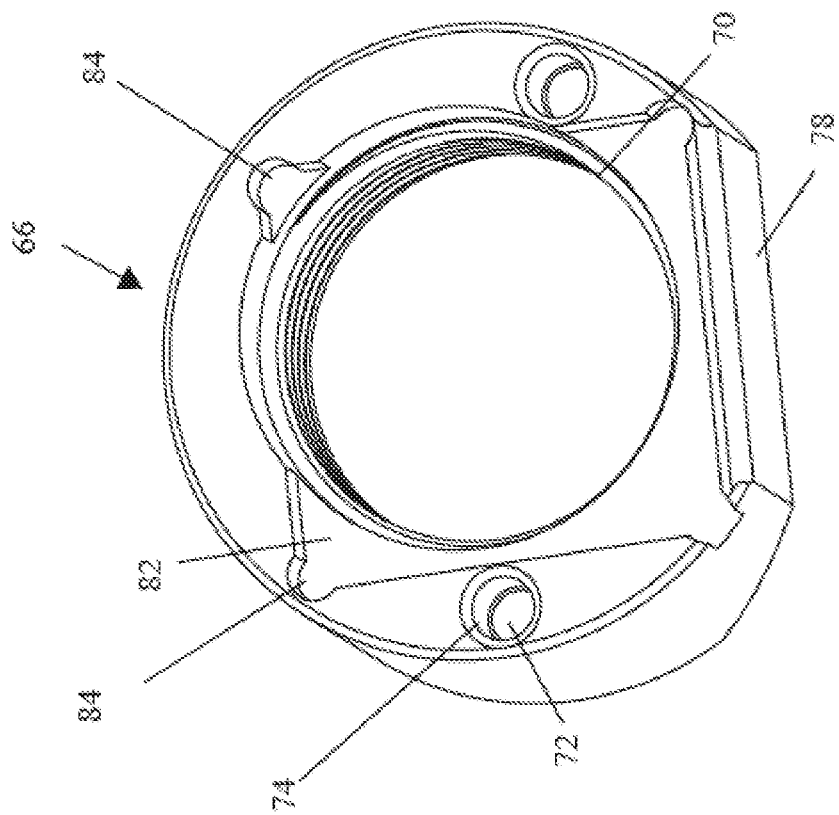
FIG. 21 is bottom perspective view of a lens mount in accordance with various embodiments of the present invention.
Figure 20:
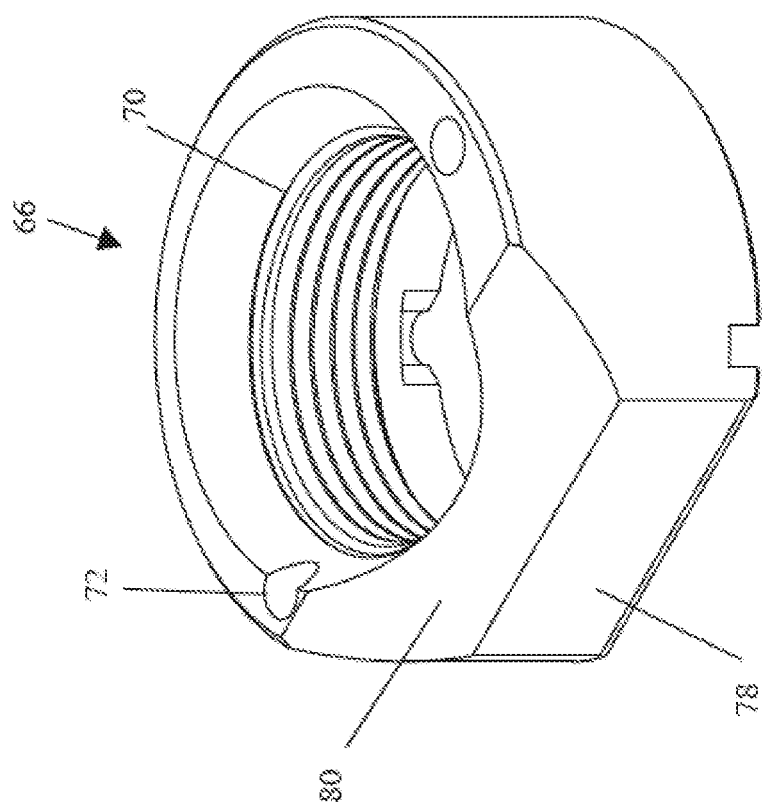
FIG. 20 is a top perspective view of a lens mount in accordance with various embodiments of the present invention.
Figure 23:
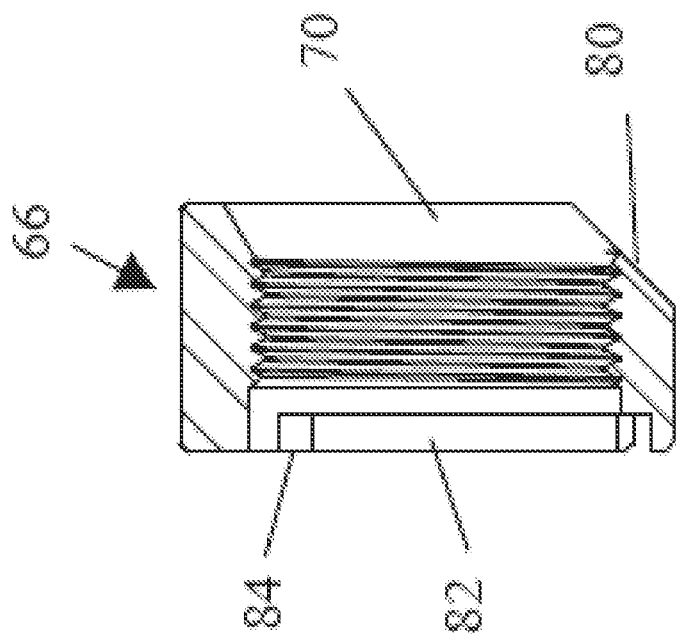
FIG. 23 is a cross-sectional view taken along line 23-23 of FIG. 22 of a lens mount in accordance with various embodiments of the present invention.
Figure 22:
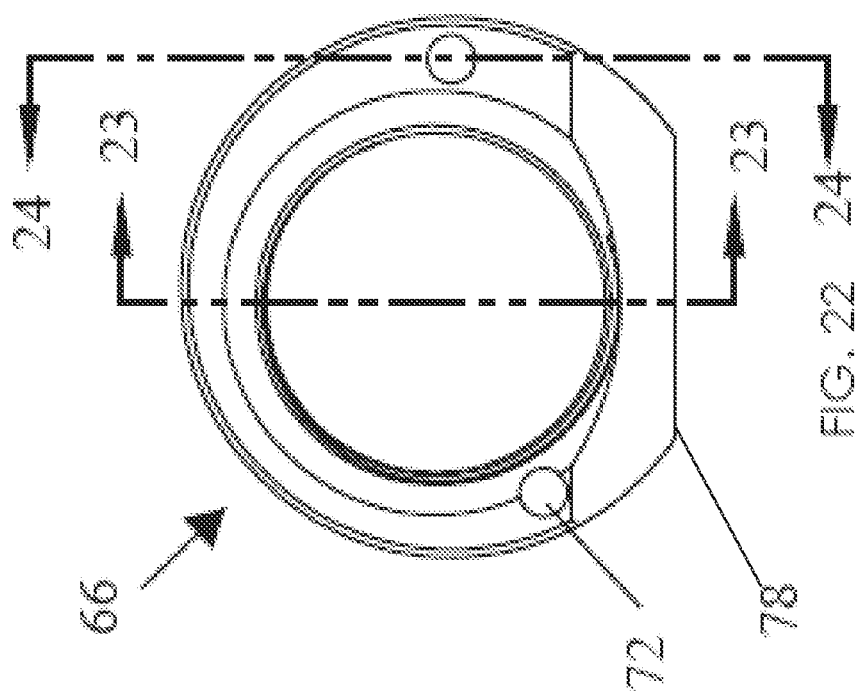
FIG. 22 is a top view of a lens mount in accordance with various embodiments of the present invention.
Figure 24:
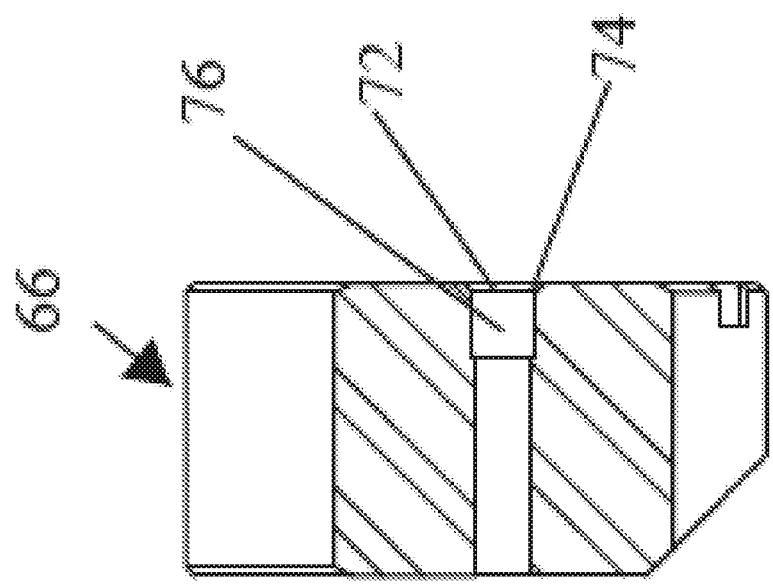
FIG. 24 is a cross-sectional view taken along line 24-24 of FIG. 22 of a lens mount in accordance with various embodiments of the present invention.
Figure 28:
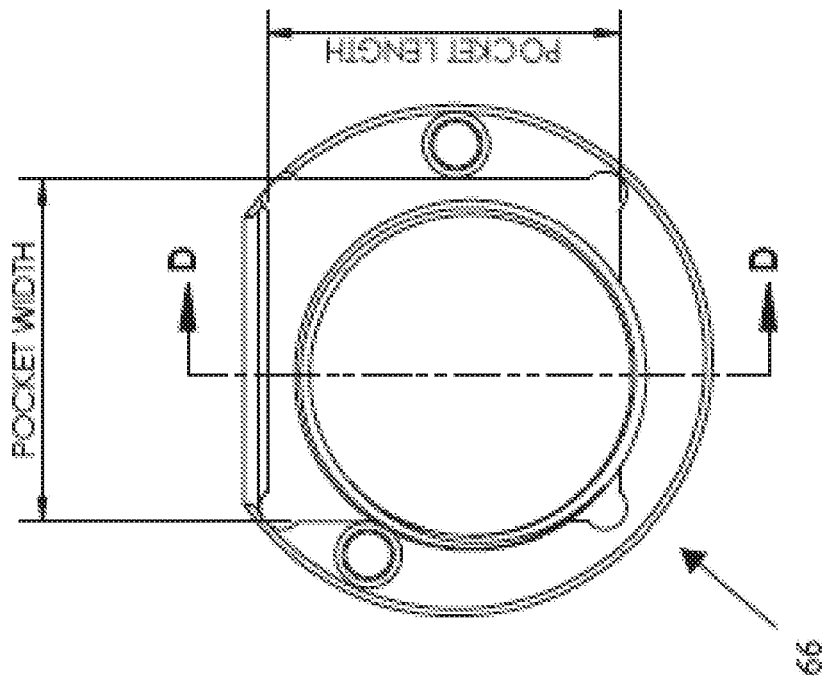
FIG. 28 is an end view of a lens mount in accordance with various embodiments of the present invention.
Figure 27:
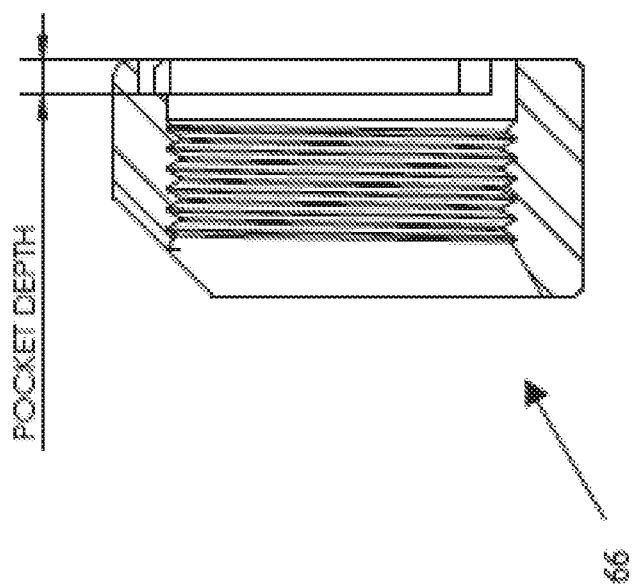
FIG. 27 is a cross-sectional view taken along line D-D of FIG. 28 of a lens mount in accordance with various embodiments of the present invention.

With particular reference to FIGS. 20-28, there is shown the lens mount 66. The lens mount 66 includes a proximal end and a distal end interconnected by a sidewall. The lens mount 66 includes a central lumen 70 extending between an opening at the proximal end and an opening at the distal end. The lens mount 66 is partially cylindrical and is sized to fit closely within the lumen of the elongated shaft 14. The central lumen 70 includes a threaded inner surface for engaging the threads on the outer surface of the lens housing 64 such that, when threaded into the lens mount 66, the lens 62 moves along the longitudinal axis. The lens mount 66 includes two pin holes 72 that extend between the proximal end and the distal end. The pin holes 72 are sized and configured to receive a dowel 36 or pin 36' in each pin hole 72. Each pin hole 72 includes a beveled entry 74 at the proximal end of the pin hole 72 as can be seen in FIGS. 21 and 24. The beveled entry 74 is a ramped or tapered entryway of greater diameter to facilitate insertion of a dowel 36 or pin 36' into the pin hole 72. A portion 76 of the length of the pin hole 72 has a larger diameter relative to the remaining length of the pin hole 72 that is distal to the larger diameter portion 76 as can be seen in FIG. 24. The beveled entry 74 has a diameter larger than the diameter of portion 76, which has a diameter larger than the rest of the pin hole 72. The enlarged diameter portion 76 allows the dowel 36 or pin 36' to be located within the enlarged diameter portion 76 before deeper insertion into the pin hole 72 allowing for the lens mount 66 to be located and set in position within the elongated shaft 14. The sidewall of the lens mount 66 includes a flat portion 78. The flat portion 78 transitions to a bevel 80 at the intersection of the flat portion 78 with the distal end. Together, the flat portion 78 and bevel 80 provide room and a smooth transition for the flexboard 26 as it bends approximately 90 degrees and extends in juxtaposition to the flat portion 78. The proximal end of the lens mount 66 includes a recess 82 that is also called a pocket. The recess 82 is a surface that is a planar notched depression into the proximal end in the shape of the sensor 24 and sized slightly larger than the sensor 24 in order to form a receiving location for the sensor 24. The recess 82 encompasses the proximal opening of the central lumen 70. The recess 82 is slightly offset and not coaxial with the proximal opening of the central lumen 70 in order to align the active image area 60 of the sensor 26 with the axis of the optical train of the lens 62. The shape of the recess 82 matches the shape of the sensor 24. The recess 82 is a square, rectangle, parallelogram or other shape. The recess 82 includes radiused corners 84 with radii on the exterior of the corner as shown in FIGS.

25-26. Not all of the corners are radiused as at least one corner is outside the sidewall perimeter. The radiused corners 84 allow the sensor to closely fit within the recess 82 such that at least a portion of the perimeter edges of the sensor 24 is in juxtaposition with the four sides of the recess 82. In one variation shown in the figures, not all of the four sides of the recess 82 are straight. At least two sides of the recess 82 are curved sharing the curvature of the lumen opening at the proximal end as can be seen in FIG. 25. The depth of the recess 82 or pocket depth is approximately 0.024 inches. When a sensor 24 is located inside the recess 82 translation of the sensor 24 laterally with respect to the longitudinal axis is prevented.

Still referencing FIG. 6, the lens assembly 18 includes a cover glass 68. The cover glass 68 is a glass disc that covers the distal opening of the elongated shaft 14. The cover glass can be made of sapphire crystal to prevent scratching, Gorilla Glass, alkali-aluminosilicate sheet glass, to prevent impact and coated borosilicate to reduce reflections depending on which properties of the glass are more important. For example, sapphire crystal protects against accidental scratching but it is more brittle and can break on impact. Gorilla Glass resists impacts but can be scratched. Coated borosilicate can mitigate reflections of the LEDs into the sensor. The cover glass 68 prevents damage to the internal components of the elongated shaft 14 especially the lens since it can scratch easily and is located at the distal tip. The cover glass 68 also prevents particulate matter from migrating into the elongated shaft 14 and obscuring the lens.

In accordance with various embodiments, to assemble the scope 10, two pins 36 or dowels 36' are inserted into the two pin holes 72 in the lens mount 66. In various embodiments, only the tapered portion 86 of pins 36 are inserted into the larger diameter portion 76 of each pin hole 72. The sensor mount 30 is aligned to bring the opposite ends of the pins 36 into the enlarged portion 40 of pin holes 34 formed in the distal end of the sensor mount 30. A pin alignment fixture, in various embodiments, that holds the sensor mount 30 and the lens mount 66 in position is used. The pins 36 that are partially inserted in their respective pin holes 34, 72 keep the sensor mount 30 and the lens mount 66 spaced apart for further assembly and alignment. The sensor 24 is soldered to electrically connect the sensor 24 to the flexboard 26. A portion of the flexboard 26 with the attached sensor 24 is then positioned between the sensor mount 30 and the lens mount 66 while the sensor mount 30 and lens mount 66 are held in a spaced-apart position by the alignment fixture. The sensor 24 is aligned and placed inside the recess 82 formed in the proximal end of the lens mount 66. The sensor mount 30 and lens mount 66 are coupled together with the distal end of the sensor 24 located in the pocket 82 and facing the lens 62 while the proximal end of the sensor 24 is attached to the sensor location 54 of the flexboard 26. The sensor location 54 is planar and substantially perpendicular to the longitudinal axis of the elongated shaft 14. The proximal end of the sensor location 54 of the flexboard 26 is supported by the distal end of the sensor mount 30. The flexboard 26 is then bent around the flat portion 50 of the sidewall and bevel 52 of the sensor mount 30. Distally, the flexboard 26 is bent under the flat portion 78 and around the bevel 80 of the lens mount 66.

In various embodiments, an optical system, e.g., the sensor mount 30 and lens mount 66 together with flexboard 26, sensor 24 and pins 36 are inserted into the elongated shaft 14. A long screwdriver or the like is used to engage the groove 42 at the proximal end of the sensor mount 30. The traverse pin hole 44 is aligned with an opening in the shaft 14 and a pin 32 is inserted into the pin hole 44 to lock the sensor mount 30 and associated lens mount 66 in position. The indexing pin 32 not only prevents longitudinal translation of the assembly, but also, prevents rotation of the assembly around the longitudinal axis of the shaft 14.

In accordance with various embodiments, the elongated shaft 14 is connected to one side of the handle 12. A receiving slot on the elongated shaft 14 is aligned with a tab formed on the inside of the handle 12. A clamp is positioned over the shaft 14 and tightened to permit movement of the shaft 14 with respect to the handle 12. The shaft 14 is permitted to rotate in order to ensure that the horizon line of an image captured by the scope 10 is level, horizontal with respect to a vertical orientation of the handle 12. The flexboard 26 and other wiring are connected to the PCBA 20 to create a functioning scope. To electrically connect the flexboard 26 to the PCBA 20, the flexboard 26 is attached by a 30-pin connector to the controller PCBA. The controller PCBA 20 has a CX3 microcontroller that supports YUV422 image format, provides $I^2C$ communications and supports MIPI Camera Serial Interface 2. The controller PCBA 20 also provides USB communication out to a monitor, regulates five voltage levels, and provides three different clock speeds for the microcontroller and image sensor. Firmware was written to provide the USB communication and to set the settings for the image sensor to meet the image requirements referred to previously. The scope 10 is then fitted with a USB cable that outputs the image to a video display, laparoscopic trainer or monitor.

In accordance with various embodiments, the shaft 14 and one side of the handle 12 is placed into an optical alignment fixture. The fixture, in various embodiments, has two towers and a toggle clamp. A target is illuminated and the scope 10 is connected to a computer monitor in order to observe an image of the target. The shaft 14 is rotated with respect to the handle 12 until the horizon becomes level, horizontal and then the toggle clamp is used to fix the position of the shaft 14. The handle 12 is then adjusted, rotated with respect to the shaft 14 until the handle 12 is vertical. The tube clamp is then tightened completely.

In various embodiments, after the assembly of the handle 12 is completed, the handle 12 and shaft 14 are placed into a press fixture. The other side of the handle clamshell is aligned in the fixture and the two halves of the handle 12 are pressed together to complete the handle and shaft assembly.

In accordance with various embodiments, the scope 10 is optically tuned by placing the scope into an optical alignment fixture. An optical target is provided and mounted into a slider movable along a rail in front of the distal end of scope 10 along the longitudinal axis of the shaft 12. The target is illuminated. The target is moved and aligned with the working distance of the lens. Then, an instrument is used to engage the socket 88 at the distal end of the lens housing 64 in order to rotate the lens housing 64 with the lens 62 inside. As the lens housing 64 is rotated, it is threadingly moved proximally or distally along the longitudinal axis with respect to the lens mount 66 to bring the image into focus. The position of the lens housing 64 with respect to the lens mount 66 is adjusted along the longitudinal axis until a middle "0" target is in acceptable focus. Focus should be acceptable through a depth-of-field range of approximately 140 mm with approximately ⅓ of that distance in front of the optimal focal plane and approximately ⅔ of that distance in back of the optimal focal plane. With the target image in focus, rotation of the lens housing 64 and tuning is finished.

After the scope 10 is optically tuned, in accordance with various embodiments, the cover glass 68 is attached to the shaft 14. The cover glass 68 is placed against the ring of LEDs connected to the flexboard 26. The cover glass 68 is then glued at four equally spaced locations to the shaft 14. Ultraviolet light is used to partially cure the adhesive. The position of the cover glass 68 is checked and, if the position is correct, the adhesive is exposed to more ultraviolet light to finish curing the adhesive. If the cover glass 68 is not in a correct position, it is readjusted while the adhesive remains partially cured.

Figure 29:
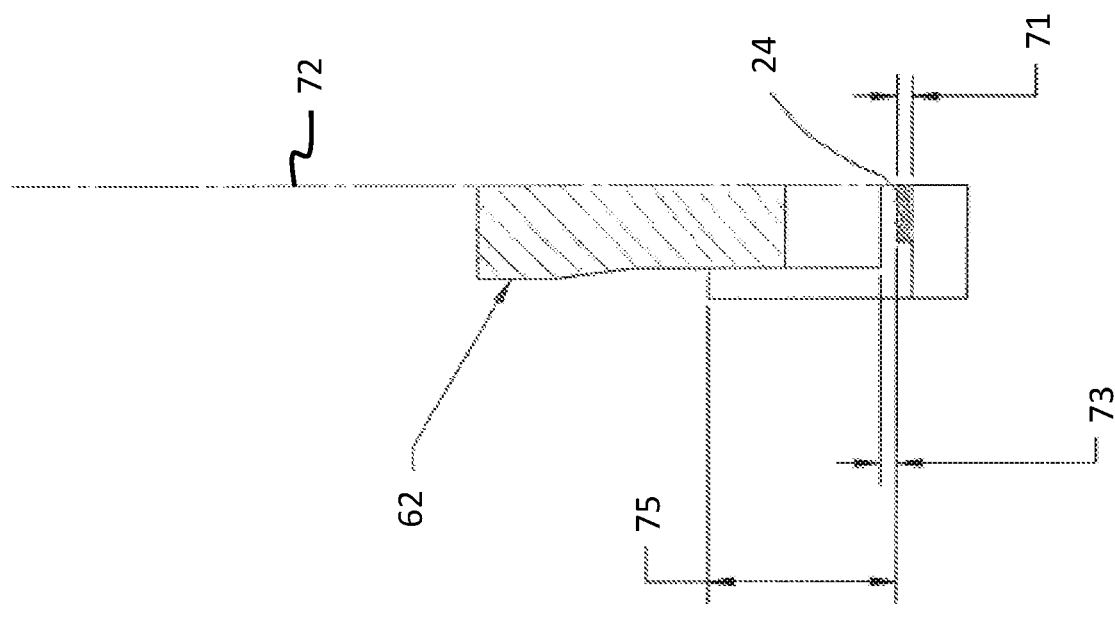
FIG. 29 is a partial schematic of a lens and sensor arrangement in accordance with various embodiments of the present invention.

In accordance with various embodiments, the lens mount 66 includes a recessed pocket 82, also referred to as a recess, having a known depth. When the sensor 24 is placed in the pocket 82, it is located radially with respect to the shaft 14. Also, the depth of the pocket 82 within the lens mount 66 has a predetermined distance to the front of the lens mount 66. This distance effectively meets all magnification, working distance and depth-of-field requirements. Any tolerances found in the sensor or its electronics are accommodated by the varying distance between the lens mount 66 and sensor mount 30 as they sandwich the image sensor 24 and electronics. This simplifies assembly as the components fit with respect to each other in only one way with the sensor 24 always at a known distance from the end of the lens mount 66. Because of this, the adjustment of the lens housing 64 to optically tune the system is made easier. Otherwise, the need to tune the optics can vary from assembly to assembly because individual components have associated tolerances. When placed in relation to other components these tolerances can stack-up making tuning more difficult and leading to out-of-focus images. Tuning is also necessary as the distance from the backside of the lens to the image sensor affects magnification, working distance and the depth-of-field. The scope 10, in accordance with various embodiments, mitigates the tolerance stack-up issue. For example, as schematically illustrated in FIG. 29, the sensor 24 and lens 62 are shown relative to the longitudinal axis 72 and the tolerance 75 between the components is enhanced or otherwise maximized. In accordance with various embodiments, the thickness 71 of sensor 24 doesn't affect the tolerance stack-up as the top of the sensor remains in the same or fixed spot relative to the threaded side of the lens mount and the thickness 73 between the sensor and lens mount also doesn't affect the stack-up. In accordance with various embodiments, the sensor and/or lens mounts are configured to ensure the location of the sensor is within the depth of focus of the lens is maintained while not damaging the sensor. The sensor mount in various embodiments is configured to remove the unpredictability, difficulties and/or complexity in the coupling of the lens mount with the sensor mount with the sensor and connector there between.

Figure 31:
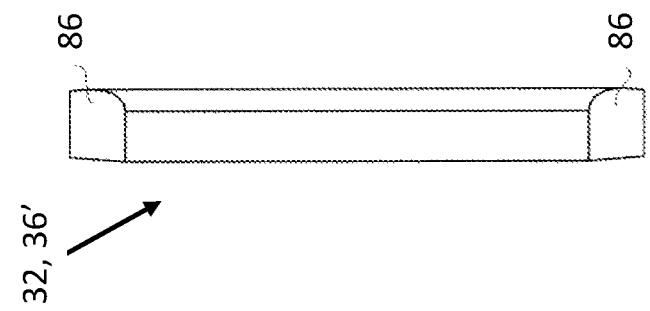
FIG. 31 is a top view of a pin in accordance with various embodiments of the present invention.
Figure 30:
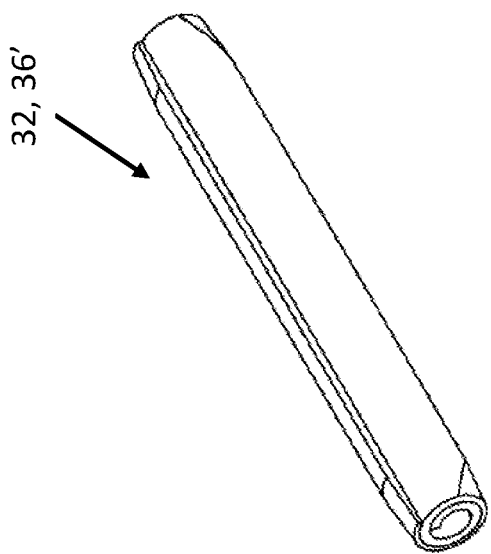
FIG. 30 is a perspective view of a pin in accordance with various embodiments of the present invention.

In FIGS. 30-31, there is shown a pin 32, 36' according to various embodiments of the present invention. In various embodiments, the pin 36' replaces the dowel 36. The pin 32, 36' is a spring pin that is rolled about itself and made of sufficiently flexible material to have a variable diameter. When compressed, the spring pin 32, 36', also called a roll pin, has a smaller diameter relative to when the spring pin 36' is relaxed. This variation in diameter assists insertion of the pin 32, 36' into pin holes 34 and 44, 72, respectively. When in a small diameter, compressed configuration, the pin 32, 36' can be easily inserted into the pin holes 34, 44 and when relaxed the relatively enlarged diameter assists in fixing the pin 32, 36' in place. The distal ends of the each pin 32, 36' include a slight taper 86.

In various embodiments, the scope has an elongated shaft that is connected to a handle at the proximal end. The shaft is long enough so that the distal end of the scope, which is the image acquisition end, is disposed inside the body cavity while the handle resides outside the patient. A scope includes an image sensor located behind a lens. The image sensor is connected to a controller printed circuit board assembly (PCBA) that includes a microcontroller configured to process data acquired by the image sensor, which is displayed on the monitor. The PCBA may be connected to the monitor or other device wirelessly or with a wire, cable or the like. Lights, such as LEDs or a fiber optic light source that transmits light through one or more fiber optic cables to the distal end of the scope, are included and connected to the scope and flexboard and/or controller PCBA to illuminate the surgical field. The lights are typically arranged in a circular fashion around the image acquisition end of the scope. One or more lenses are included in the optical assembly to focus the light reflected off the surgical site.

In order for the simulation surgical scopes in accordance with various embodiments of the present invention to be suitable or effective for training or simulation purposes, the scopes should meet one or more certain criteria. For example, the ergonomics of the scope should be similar to surgical-grade scopes. The size and shape of the handle, the length of the shaft as well as the weight of the scope should approximate a surgical-grade scope. Also, the simulation surgical scope should be capable of being manipulated by one hand. The scope should also be able to withstand accidental bumps and drops without breaking or losing functionality. Also, in order for users to learn and get comfortable with medical device trocars and the like, a simulation surgical scope should be sized and configured to be compatible with and fit inside medical device trocars that are used in surgery. Typically, there are two sizes of trocars, 10 mm and 5 mm, that are used as a port for passing a scope to the surgical site. Therefore, a simulation surgical scope should be at least be compatible with either a 10 mm and/or 5 mm trocar.

The simulation surgical scope in accordance with various embodiments does not need to be made to withstand repeated sterilization, cleaning and autoclave cycles. As such, the scope can be less expensive. While lighting on the scope can be required for certain procedure simulations, the light source at the tip of the scope in some instances can be supplemented by other light sources installed inside the cavity of the box trainer. Therefore, the lighting demands for a surgical simulation scope is reduced which may further lower manufacturing costs of the scope. Also, with respect to the optical performance, the simulation surgical scope in accordance with various embodiments may sacrifice some image quality and include some distortion at the edges of the image by using less expensive components and a simpler lens assembly design. Overall, the image quality should be sufficient enough to provide an appropriate amount of detail in order to distinguish the subtle differences in simulated anatomy. Since the requirements for image quality and lighting at the tip for a surgical simulation scope are not as stringent as that for a surgical-grade scope and there is no requirement for sterility, it is possible to keep the cost lower than that of surgical-grade scopes. A simulation surgical scope, in accordance with various embodiments, should have the balance of a quality image, working distance and depth-of-field, low cost, and/or robustness to last for a multitude of uses. These desired attributes can be connected and optimally designing a scope for one of these attributes may make meeting another attribute more difficult.

The surgical simulation scope in accordance with various embodiments is suitable for use with laparoscopic trainers to educate and train medical professionals and medical students. The surgical simulation scope in accordance with various embodiments provides significant improvements that may also be employed in surgical-grade scopes.

In various embodiments, a simulation surgical camera scope is provided comprising at least one of a lens mount and/or a sensor mount and in accordance with various embodiments, other embodiments, portions of such embodiments and/or any combination thereof described throughout the description can be combined with such a simulation surgical camera scope. In various embodiments, the simulation surgical camera scope further comprises at least one of a handle, an elongate shaft, an image sensor, a flexible circuit board and a lens. In various embodiments, a simulation surgical camera scope is provided comprising a lens mount having a pocket therein. In various embodiments, a simulation surgical camera scope is provided comprising a sensor mount having a flat surface. In various embodiments, a simulation surgical camera scope is provided comprising a sensor mount having a flat surface adjacent to a raised surface. In various embodiments, the simulation surgical camera scope comprises at least one of a lens mount, a sensor mount, a handle, an elongate shaft, an image sensor, a flexible circuit board, a lens. In various embodiments, the simulation surgical camera scope comprises a lens mount, a sensor mount, a handle, an elongate shaft, an image sensor, a flexible circuit board, a lens or any combination thereof.

The above description is provided to enable any person skilled in the art to make and use the camera scopes and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A simulation surgical camera scope comprising:
   a handle that houses a controller;
   an elongate shaft having a proximal end coupled to the handle and a distal end comprising:
      a sensor mount, and
      a lens mount, the lens mount having a proximal portion having a pocket therein, wherein the pocket is a notched depression in a proximal end of the proximal portion of the lens mount;
      a lens disposed within the lens mount; and
      an image sensor disposed within the pocket of the lens mount, the image sensor having a distal face facing the distal end of the elongate shaft,
      wherein the pocket has at least one radiused corner configured to allow the image sensor to have at least a portion of a perimeter of the image sensor to be in juxtaposition with one or more sides of the pocket.

2. The simulation surgical camera scope of claim 1 wherein the image sensor is disposed between the lens mount and the sensor mount.

3. The simulation surgical camera scope of claim 1 wherein the lens mount is disposed between the distal end of the elongate shaft and the sensor mount.

4. The simulation surgical camera scope of claim 3 wherein the sensor mount has a distal portion with a flat surface disposed between a pair of raised surfaces, the pair of raised surfaces acting as a hard stop to prevent crushing of the image sensor.

5. The simulation surgical camera scope of claim 4 wherein the pair of raised surfaces have a length smaller than a thickness of the image sensor.

6. The simulation surgical camera scope of claim 4 further comprising a lens housing, wherein the lens mount has a threaded portion and the lens housing has corresponding threads, the lens housing being configured to be threaded into the lens mount and allowing the lens housing to rotate for optically tuning the lens.

7. The simulation surgical camera scope of claim 4, wherein the flat surface and the pair of raised surfaces delimit a channel having a depth smaller than a thickness of the image sensor.

8. The simulation surgical camera scope of claim 4, wherein the pocket of the lens mount has a depth smaller than a thickness of the image sensor.

9. The simulation surgical camera scope of claim 4 wherein the flat surface of the sensor mount has a width equal to or greater than a width of the image sensor.

10. The simulation surgical camera scope of claim 9 wherein the flat surface of the sensor mount has a height equal to or greater than a height of the image sensor.

11. The simulation surgical camera scope of claim 1 wherein the lens has a proximal face and the distal face of the image sensor faces the proximal face of the lens.

12. The simulation surgical camera scope of claim 1 further comprising a flexible printed circuit board extending from the distal end of the elongate shaft to the proximal end of the elongate shaft and following a path starting from a distal end of the lens mount, between the lens mount and the sensor mount, past a distal end of the sensor mount and to the proximal end of the elongate shaft.

13. A simulation surgical camera scope comprising:
   a handle;
   an elongate shaft having a proximal end coupled to the handle and a distal end comprising a sensor mount and a lens mount, the elongate shaft having a longitudinal axis extending from the proximal end of the elongate shaft to the distal end of the elongate shaft;
   a lens disposed within the lens mount, wherein a proximal portion of the lens mount has a pocket, the pocket being a notched depression in a proximal end of the proximal portion of the lens mount; and
   an image sensor disposed between the sensor mount and the lens mount, the lens mount having a proximal end and a distal end, the proximal end of the lens mount being parallel to the distal end of the lens mount and the sensor mount having a proximal end and a distal end, the proximal end of the sensor mount being parallel to the distal end of the sensor mount and the proximal end of the lens mount and orthogonal to the longitudinal axis of the elongate shaft,
   wherein the pocket has at least one radiused corner configured to allow the image sensor to have at least a portion of a perimeter of the image sensor to be in juxtaposition with one or more sides of the pocket.

14. The simulation surgical camera scope of claim 13 wherein the elongate shaft is fixed to the handle to be non-rotatable relative to the handle and wherein the sensor mount in its entirety is positioned proximally from the lens mount.

15. The simulation surgical camera scope of claim 13 further comprising a flexible printed circuit board connected to a controller housed in the handle and extends from the distal end of the elongate shaft before the distal end of the lens mount, between the sensor and lens mount and to the proximal end of the elongate shaft.

16. The simulation surgical camera scope of claim 15 wherein the lens mount has a distal surface on the distal end of the lens mount, the distal surface having a flat portion and a bevel.

17. The simulation surgical camera scope of claim 16 wherein the sensor mount has a proximal surface on the proximal end of the sensor mount, the proximal surface having a flat portion and a bevel.

18. The simulation surgical camera scope of claim 17 wherein a distal portion of the sensor mount has a cavity defined by a pair of raised surfaces.

19. The simulation surgical camera scope of claim 18 wherein the image sensor is disposed between the lens mount and the sensor mount between the pair of raised surfaces and within the cavity of the sensor mount to place the image sensor within the depth of focus of the lens.

20. The simulation surgical camera scope of claim 13 wherein the pocket is offset and not co-axial with a center of the lens mount.

21. A simulation surgical camera scope comprising:
a handle;
a cylindrical elongate shaft having a proximal end coupled to the handle and a distal end comprising a cylindrical sensor mount and a cylindrical lens mount, the cylindrical lens mount having threads disposed on an inner surface of the cylindrical lens mount;
a cylindrical lens connected to a lens housing having threads disposed on an outer surface of the lens housing and arranged to mate with the threads of the cylindrical lens mount, the cylindrical lens mount having a pocket, a center aperture and at least one pin hole positioned next to the pocket, wherein the pocket is a notched depression in a proximal end of the proximal portion of the cylindrical lens mount; and
an image sensor disposed within the pocket of the cylindrical lens mount and between the cylindrical sensor mount and a distal end of the cylindrical lens mount, the cylindrical sensor mount having a cavity defined by a pair of raised surfaces, at least one of the pair of raised surface having at least one pin hole, the at least one pin hole of the cylindrical lens mount being aligned with the at least one pin hole of the cylindrical sensor mount, wherein the pocket has at least one radiused corner configured to allow the image sensor to have at least a portion of a perimeter of the image sensor to be in juxtaposition with one or more sides of the pocket.

22. The simulation surgical camera scope of claim 21, wherein the cylindrical sensor mount further comprises an angled pinhole extending in an angled direction relative to the at least one pin hole of the cylindrical sensor mount extending longitudinally and not aligned with the at least one pin hole of the cylindrical lens mount, the angled pinhole configured to align and set a position of the cylindrical sensor mount with respect to the cylindrical elongate shaft.

* * * * *